United States Patent
Stefanchik et al.

(10) Patent No.: US 8,070,759 B2
(45) Date of Patent: Dec. 6, 2011

(54) SURGICAL FASTENING DEVICE

(75) Inventors: David Stefanchik, Morrow, OH (US); James T. Spivey, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 543 days.

(21) Appl. No.: 12/130,023

(22) Filed: May 30, 2008

(65) Prior Publication Data

US 2009/0299385 A1    Dec. 3, 2009

(51) Int. Cl.
*A61B 17/10* (2006.01)

(52) U.S. Cl. ...................................................... 606/139

(58) Field of Classification Search .................. 606/139, 606/142, 143, 157, 205–211, 213, 144–151, 606/219–221, 228; 623/23.72–23.74; 433/3, 433/4; 227/175.1
See application file for complete search history.

(56) References Cited

U.S. PATENT DOCUMENTS

| | | |
|---|---|---|
| 645,576 A | 3/1900 | Telsa |
| 649,621 A | 5/1900 | Tesla |
| 787,412 A | 4/1905 | Tesla |
| 1,127,948 A | 2/1915 | Wappler |
| 1,482,653 A | 2/1924 | Lilly |
| 1,625,602 A | 4/1927 | Gould et al. |
| 2,028,635 A | 1/1936 | Wappler |
| 2,113,246 A | 4/1938 | Wappler |
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,493,108 A | 1/1950 | Casey, Jr. |
| 2,504,152 A | 4/1950 | Riker et al. |
| 2,938,382 A | 5/1960 | De Graaf |
| 2,952,206 A | 9/1960 | Becksted |
| 3,069,195 A | 12/1962 | Buck |
| 3,170,471 A | 2/1965 | Schnitzer |
| 3,435,824 A | 4/1969 | Gamponia |
| 3,470,876 A | 10/1969 | Barchilon |
| 3,669,487 A | 6/1972 | Roberts et al. |
| 3,746,881 A | 7/1973 | Fitch et al. |
| 3,799,672 A | 3/1974 | Vurek |
| 3,854,473 A | 12/1974 | Matsuo |
| 3,946,740 A | 3/1976 | Bassett |

(Continued)

FOREIGN PATENT DOCUMENTS

AU              666310 B2    2/1996

(Continued)

OTHER PUBLICATIONS

Michael S. Kavic, M.D., "Natural Orifice Translumenal Endoscopic Surgery: "NOTES"", JSLS, vol. 10, pp. 133-134 (2006).

(Continued)

*Primary Examiner* — Melanie Tyson

(57) ABSTRACT

Various embodiments are directed to a surgical device including an end effector. The end effector may include a first jaw member defining a first groove and a second jaw member defining a second groove. The first jaw member and the second jaw member may be selectively pivotable between an open position and a closed position. Also, the first groove and the second groove may align to form a combined helical groove when the first jaw member and the second jaw member are in the closed position. In addition, the first jaw member may define a wire opening aligned with the first groove. Further, the first jaw member may define a beveled edge directed distally and substantially parallel to a distal portion of the wire opening.

7 Claims, 16 Drawing Sheets

U.S. PATENT DOCUMENTS

| | | | |
|---|---|---|---|
| 3,948,251 A | 4/1976 | Hosono | |
| 3,994,301 A | 11/1976 | Agris | |
| 4,011,872 A | 3/1977 | Komiya | |
| 4,012,812 A | 3/1977 | Black | |
| 4,164,225 A | 8/1979 | Johnson et al. | |
| 4,178,920 A | 12/1979 | Cawood, Jr. et al. | |
| 4,207,873 A | 6/1980 | Kruy | |
| 4,235,238 A | 11/1980 | Ogiu et al. | |
| 4,258,716 A | 3/1981 | Sutherland | |
| 4,278,077 A | 7/1981 | Mizumoto | |
| 4,285,344 A | 8/1981 | Marshall | |
| 4,311,143 A | 1/1982 | Komiya | |
| 4,329,980 A | 5/1982 | Terada | |
| 4,396,021 A | 8/1983 | Baumgartner | |
| 4,452,246 A | 6/1984 | Bader et al. | |
| 4,461,281 A | 7/1984 | Carson | |
| 4,491,132 A | 1/1985 | Aikins | |
| 4,527,331 A | 7/1985 | Lasner et al. | |
| 4,527,564 A | 7/1985 | Eguchi et al. | |
| 4,538,594 A | 9/1985 | Boebel et al. | |
| D281,104 S | 10/1985 | Davison | |
| 4,569,347 A | 2/1986 | Frisbie | |
| 4,580,551 A | 4/1986 | Siegmund et al. | |
| 4,646,722 A | 3/1987 | Silverstein et al. | |
| 4,653,476 A | 3/1987 | Bonnet | |
| 4,669,470 A | 6/1987 | Brandfield | |
| 4,671,477 A | 6/1987 | Cullen | |
| 4,685,447 A | 8/1987 | Iversen et al. | |
| 4,711,240 A | 12/1987 | Goldwasser et al. | |
| 4,712,545 A | 12/1987 | Honkanen | |
| 4,721,116 A | 1/1988 | Schintgen et al. | |
| 4,733,662 A | 3/1988 | DeSatnick et al. | |
| D295,894 S | 5/1988 | Sharkany et al. | |
| 4,763,669 A | 8/1988 | Jaeger | |
| 4,770,188 A | 9/1988 | Chikama | |
| 4,815,450 A | 3/1989 | Patel | |
| 4,823,794 A | 4/1989 | Pierce | |
| 4,829,999 A | 5/1989 | Auth | |
| 4,873,979 A | 10/1989 | Hanna | |
| 4,880,015 A | 11/1989 | Nierman | |
| 4,911,148 A | 3/1990 | Sosnowski et al. | |
| 4,926,860 A | 5/1990 | Stice et al. | |
| 4,938,214 A | 7/1990 | Specht et al. | |
| 4,950,273 A | 8/1990 | Briggs | |
| 4,950,285 A | 8/1990 | Wilk | |
| 4,977,887 A | 12/1990 | Gouda | |
| 4,984,581 A | 1/1991 | Stice | |
| 5,007,917 A | 4/1991 | Evans | |
| 5,010,876 A | 4/1991 | Henley et al. | |
| 5,020,514 A | 6/1991 | Heckele | |
| 5,020,535 A | 6/1991 | Parker et al. | |
| 5,025,778 A | 6/1991 | Silverstein et al. | |
| 5,033,169 A | 7/1991 | Bindon | |
| 5,037,433 A | 8/1991 | Wilk et al. | |
| 5,041,129 A | 8/1991 | Hayhurst et al. | |
| 5,046,513 A | 9/1991 | Gatturna et al. | |
| 5,050,585 A | 9/1991 | Takahashi | |
| 5,052,372 A | 10/1991 | Shapiro | |
| 5,065,516 A | 11/1991 | Dulebohn | |
| 5,066,295 A | 11/1991 | Kozak et al. | |
| 5,123,913 A | 6/1992 | Wilk et al. | |
| 5,123,914 A | 6/1992 | Cope | |
| 5,133,727 A | 7/1992 | Bales et al. | |
| 5,147,374 A | 9/1992 | Fernandez | |
| 5,174,300 A | 12/1992 | Bales et al. | |
| 5,176,126 A | 1/1993 | Chikama | |
| 5,190,050 A | 3/1993 | Nitzsche | |
| 5,190,555 A | 3/1993 | Wetter et al. | |
| 5,192,284 A | 3/1993 | Pleatman | |
| 5,201,752 A | 4/1993 | Brown et al. | |
| 5,201,908 A | 4/1993 | Jones | |
| 5,203,785 A | 4/1993 | Slater | |
| 5,203,787 A | 4/1993 | Noblitt et al. | |
| 5,209,747 A | 5/1993 | Knoepfler | |
| 5,217,003 A | 6/1993 | Wilk | |
| 5,217,453 A | 6/1993 | Wilk | |
| 5,219,357 A | 6/1993 | Honkanen et al. | |
| 5,219,358 A | 6/1993 | Bendel et al. | |
| 5,222,362 A | 6/1993 | Maus et al. | |
| 5,222,965 A | 6/1993 | Haughton | |
| 5,234,437 A | 8/1993 | Sepetka | |
| 5,234,453 A | 8/1993 | Smith et al. | |
| 5,235,964 A | 8/1993 | Abenaim | |
| 5,242,456 A | 9/1993 | Nash et al. | |
| 5,246,424 A | 9/1993 | Wilk | |
| 5,259,366 A | 11/1993 | Reydel et al. | |
| 5,263,958 A | 11/1993 | deGuillebon et al. | |
| 5,273,524 A | 12/1993 | Fox et al. | |
| 5,275,607 A | 1/1994 | Lo et al. | |
| 5,284,128 A | 2/1994 | Hart | |
| 5,284,162 A | 2/1994 | Wilk | |
| 5,287,845 A | 2/1994 | Faul et al. | |
| 5,290,299 A | 3/1994 | Fain et al. | |
| 5,290,302 A | 3/1994 | Pericic | |
| 5,295,977 A | 3/1994 | Cohen et al. | |
| 5,297,536 A | 3/1994 | Wilk | |
| 5,301,061 A | 4/1994 | Nakada et al. | |
| 5,312,333 A | 5/1994 | Churinetz et al. | |
| 5,312,351 A | 5/1994 | Gerrone | |
| 5,312,416 A | 5/1994 | Spaeth et al. | |
| 5,312,423 A | 5/1994 | Rosenbluth et al. | |
| 5,320,636 A | 6/1994 | Slater | |
| 5,325,845 A | 7/1994 | Adair | |
| 5,330,471 A | 7/1994 | Eggers | |
| 5,330,486 A | 7/1994 | Wilk | |
| 5,330,488 A | 7/1994 | Goldrath | |
| 5,330,496 A | 7/1994 | Alferness | |
| 5,330,502 A | 7/1994 | Hassler et al. | |
| 5,331,971 A | 7/1994 | Bales et al. | |
| 5,334,198 A | 8/1994 | Hart et al. | |
| 5,344,428 A | 9/1994 | Griffiths | |
| 5,350,391 A | 9/1994 | Iacovelli | |
| 5,352,184 A | 10/1994 | Goldberg et al. | |
| 5,352,222 A | 10/1994 | Rydell | |
| 5,354,302 A | 10/1994 | Ko | |
| 5,354,311 A | 10/1994 | Kambin et al. | |
| 5,356,408 A | 10/1994 | Rydell | |
| 5,364,408 A | 11/1994 | Gordon | |
| 5,364,410 A | 11/1994 | Failla et al. | |
| 5,366,466 A | 11/1994 | Christian et al. | |
| 5,366,467 A | 11/1994 | Lynch et al. | |
| 5,368,605 A | 11/1994 | Miller, Jr. | |
| 5,370,647 A | 12/1994 | Graber et al. | |
| 5,374,273 A | 12/1994 | Nakao et al. | |
| 5,374,275 A | 12/1994 | Bradley et al. | |
| 5,374,277 A | 12/1994 | Hassler | |
| 5,377,695 A | 1/1995 | An Haack | |
| 5,383,877 A | 1/1995 | Clarke | |
| 5,383,888 A | 1/1995 | Zvenyatsky et al. | |
| 5,391,174 A | 2/1995 | Weston | |
| 5,392,789 A | 2/1995 | Slater et al. | |
| 5,395,386 A | 3/1995 | Slater | |
| 5,401,248 A | 3/1995 | Bencini | |
| 5,403,328 A | 4/1995 | Shallman | |
| 5,403,342 A | 4/1995 | Tovey et al. | |
| 5,403,348 A | 4/1995 | Bonutti | |
| 5,405,073 A | 4/1995 | Porter | |
| 5,405,359 A | 4/1995 | Pierce | |
| 5,409,478 A | 4/1995 | Gerry et al. | |
| 5,417,699 A | 5/1995 | Klein et al. | |
| 5,423,821 A | 6/1995 | Pasque | |
| 5,433,721 A | 7/1995 | Hooven et al. | |
| 5,439,471 A | 8/1995 | Kerr | |
| 5,439,478 A | 8/1995 | Palmer | |
| 5,441,059 A | 8/1995 | Dannan | |
| 5,441,499 A | 8/1995 | Fritzsch | |
| 5,449,021 A | 9/1995 | Chikama | |
| 5,456,667 A | 10/1995 | Ham et al. | |
| 5,456,684 A | 10/1995 | Schmidt et al. | |
| 5,458,131 A | 10/1995 | Wilk | |
| 5,458,583 A | 10/1995 | McNeely et al. | |
| 5,460,168 A | 10/1995 | Masubuchi et al. | |
| 5,460,629 A | 10/1995 | Shlain et al. | |
| 5,462,561 A | 10/1995 | Voda | |
| 5,465,731 A | 11/1995 | Bell et al. | |
| 5,467,763 A | 11/1995 | McMahon et al. | |
| 5,468,250 A | 11/1995 | Paraschac et al. | |

| Patent | Date | Inventor |
|---|---|---|
| 5,470,308 A | 11/1995 | Edwards et al. |
| 5,470,320 A | 11/1995 | Tiefenbrun et al. |
| 5,478,347 A | 12/1995 | Aranyi |
| 5,480,404 A | 1/1996 | Kammerer et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A * | 3/1996 | Schulken et al. ............. 606/144 |
| 5,499,992 A | 3/1996 | Meade et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,522,829 A | 6/1996 | Michalos |
| 5,522,830 A | 6/1996 | Aranyi |
| 5,527,321 A | 6/1996 | Hinchliffe |
| 5,540,648 A | 7/1996 | Yoon |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,591,179 A | 1/1997 | Edelstein |
| 5,593,420 A | 1/1997 | Eubanks, Jr et al. |
| 5,595,562 A | 1/1997 | Grier |
| 5,597,378 A | 1/1997 | Jervis |
| 5,601,573 A | 2/1997 | Fogelberg et al. |
| 5,601,588 A | 2/1997 | Tonomura et al. |
| 5,604,531 A | 2/1997 | Iddan et al. |
| 5,607,389 A | 3/1997 | Edwards et al. |
| 5,607,450 A | 3/1997 | Zvenyatsky et al. |
| 5,613,975 A | 3/1997 | Christy |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,628,732 A | 5/1997 | Antoon, Jr. et al. |
| 5,630,782 A | 5/1997 | Adair |
| 5,643,283 A | 7/1997 | Younker |
| 5,643,292 A | 7/1997 | Hart |
| 5,643,294 A | 7/1997 | Tovey et al. |
| 5,644,798 A | 7/1997 | Shah |
| 5,645,083 A | 7/1997 | Essig et al. |
| 5,649,372 A | 7/1997 | Souza |
| 5,653,677 A | 8/1997 | Okada et al. |
| 5,653,722 A | 8/1997 | Kieturakis |
| 5,662,663 A | 9/1997 | Shallman |
| 5,669,875 A | 9/1997 | van Eerdenburg |
| 5,681,324 A | 10/1997 | Kammerer et al. |
| 5,681,330 A | 10/1997 | Hughett et al. |
| 5,685,820 A | 11/1997 | Riek et al. |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |
| 5,704,892 A | 1/1998 | Adair |
| 5,709,708 A | 1/1998 | Thal |
| 5,716,326 A | 2/1998 | Dannan |
| 5,730,740 A | 3/1998 | Wales et al. |
| 5,741,278 A | 4/1998 | Stevens |
| 5,741,285 A | 4/1998 | McBrayer et al. |
| 5,746,759 A | 5/1998 | Meade et al. |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,779,701 A | 7/1998 | McBrayer et al. |
| 5,779,716 A | 7/1998 | Cano et al. |
| 5,779,727 A | 7/1998 | Orejola |
| 5,782,859 A | 7/1998 | Nicholas et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,803,903 A | 9/1998 | Athas et al. |
| 5,808,665 A | 9/1998 | Green |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,058 A | 9/1998 | Carlson et al. |
| 5,817,061 A | 10/1998 | Goodwin et al. |
| 5,817,107 A | 10/1998 | Schaller |
| 5,817,119 A | 10/1998 | Klieman et al. |
| 5,819,736 A | 10/1998 | Avny et al. |
| 5,827,281 A | 10/1998 | Levin |
| 5,827,299 A | 10/1998 | Thomason et al. |
| 5,830,231 A | 11/1998 | Geiges, Jr. |
| 5,833,700 A | 11/1998 | Fogelberg et al. |
| 5,833,703 A | 11/1998 | Manushakian |
| 5,843,017 A | 12/1998 | Yoon |
| 5,849,022 A | 12/1998 | Sakashita et al. |
| 5,853,374 A | 12/1998 | Hart et al. |
| 5,855,585 A | 1/1999 | Kontos |
| 5,860,913 A | 1/1999 | Yamaya et al. |
| 5,860,995 A | 1/1999 | Berkelaar |
| 5,868,762 A | 2/1999 | Cragg et al. |
| 5,876,411 A | 3/1999 | Kontos |
| 5,882,331 A | 3/1999 | Sasaki |
| 5,882,344 A | 3/1999 | Stouder, Jr. |
| 5,893,846 A | 4/1999 | Bales et al. |
| 5,893,874 A | 4/1999 | Bourque et al. |
| 5,893,875 A | 4/1999 | O'Connor et al. |
| 5,899,919 A | 5/1999 | Eubanks, Jr. et al. |
| 5,902,254 A | 5/1999 | Magram |
| 5,904,702 A | 5/1999 | Ek et al. |
| 5,908,420 A | 6/1999 | Parins et al. |
| 5,916,147 A | 6/1999 | Boury |
| 5,921,993 A | 7/1999 | Yoon |
| 5,921,997 A | 7/1999 | Fogelberg et al. |
| 5,922,008 A | 7/1999 | Gimpelson |
| 5,925,052 A | 7/1999 | Simmons |
| 5,928,255 A | 7/1999 | Meade et al. |
| 5,928,266 A | 7/1999 | Kontos |
| 5,936,536 A | 8/1999 | Morris |
| 5,944,718 A | 8/1999 | Austin et al. |
| 5,951,549 A | 9/1999 | Richardson et al. |
| 5,954,720 A | 9/1999 | Wilson et al. |
| 5,954,731 A | 9/1999 | Yoon |
| 5,957,943 A | 9/1999 | Vaitekunas |
| 5,957,953 A | 9/1999 | DiPoto et al. |
| 5,971,995 A | 10/1999 | Rousseau |
| 5,976,074 A | 11/1999 | Moriyama |
| 5,976,075 A | 11/1999 | Beane et al. |
| 5,976,130 A | 11/1999 | McBrayer et al. |
| 5,976,131 A | 11/1999 | Guglielmi et al. |
| 5,980,539 A | 11/1999 | Kontos |
| 5,980,556 A | 11/1999 | Giordano et al. |
| 5,984,938 A | 11/1999 | Yoon |
| 5,989,182 A | 11/1999 | Hori et al. |
| 5,993,447 A | 11/1999 | Blewett et al. |
| 5,997,555 A | 12/1999 | Kontos |
| 6,001,120 A | 12/1999 | Levin |
| 6,004,330 A | 12/1999 | Middleman et al. |
| 6,007,566 A | 12/1999 | Wenstrom, Jr. |
| 6,010,515 A | 1/2000 | Swain et al. |

| Patent | Date | Inventor |
|---|---|---|
| 6,012,494 A | 1/2000 | Balazs |
| 6,019,770 A | 2/2000 | Christoudias |
| 6,024,708 A | 2/2000 | Bales et al. |
| 6,024,747 A | 2/2000 | Kontos |
| 6,027,522 A | 2/2000 | Palmer |
| 6,030,365 A | 2/2000 | Laufer |
| 6,033,399 A | 3/2000 | Gines |
| 6,053,927 A | 4/2000 | Hamas |
| 6,066,160 A | 5/2000 | Colvin et al. |
| 6,068,603 A | 5/2000 | Suzuki |
| 6,068,629 A | 5/2000 | Haissaguerre et al. |
| 6,071,233 A | 6/2000 | Ishikawa et al. |
| 6,074,408 A | 6/2000 | Freeman |
| 6,086,530 A | 7/2000 | Mack |
| 6,090,108 A | 7/2000 | McBrayer et al. |
| 6,096,046 A | 8/2000 | Weiss |
| 6,110,154 A | 8/2000 | Shimomura et al. |
| 6,110,183 A | 8/2000 | Cope |
| 6,113,593 A | 9/2000 | Tu et al. |
| 6,117,144 A | 9/2000 | Nobles et al. |
| 6,117,158 A | 9/2000 | Measamer et al. |
| 6,139,555 A | 10/2000 | Hart et al. |
| 6,146,391 A | 11/2000 | Cigaina |
| 6,149,653 A | 11/2000 | Deslauriers |
| 6,149,662 A | 11/2000 | Pugliesi et al. |
| 6,159,200 A | 12/2000 | Verdura et al. |
| 6,165,184 A | 12/2000 | Verdura et al. |
| 6,168,570 B1 | 1/2001 | Ferrera |
| 6,168,605 B1 | 1/2001 | Measamer et al. |
| 6,170,130 B1 | 1/2001 | Hamilton et al. |
| 6,179,776 B1 | 1/2001 | Adams et al. |
| 6,179,837 B1 | 1/2001 | Hooven |
| 6,183,420 B1 | 2/2001 | Douk et al. |
| 6,190,353 B1 | 2/2001 | Makower et al. |
| 6,190,384 B1 | 2/2001 | Ouchi |
| 6,190,399 B1 | 2/2001 | Palmer et al. |
| 6,203,533 B1 | 3/2001 | Ouchi |
| 6,206,872 B1 | 3/2001 | Lafond et al. |
| 6,206,877 B1 | 3/2001 | Kese et al. |
| 6,214,007 B1 | 4/2001 | Anderson |
| 6,228,096 B1 | 5/2001 | Marchand |
| 6,245,079 B1 | 6/2001 | Nobles et al. |
| 6,246,914 B1 | 6/2001 | de la Rama et al. |
| 6,258,064 B1 | 7/2001 | Smith et al. |
| 6,261,242 B1 | 7/2001 | Roberts et al. |
| 6,264,664 B1 | 7/2001 | Avellanet |
| 6,270,497 B1 | 8/2001 | Sekino et al. |
| 6,270,505 B1 | 8/2001 | Yoshida et al. |
| 6,277,136 B1 | 8/2001 | Bonutti |
| 6,283,963 B1 | 9/2001 | Regula |
| 6,293,909 B1 | 9/2001 | Chu et al. |
| 6,293,952 B1 | 9/2001 | Brosens et al. |
| 6,296,630 B1 | 10/2001 | Altman et al. |
| 6,322,578 B1 | 11/2001 | Houle et al. |
| 6,326,177 B1 | 12/2001 | Schoenbach et al. |
| 6,328,730 B1 | 12/2001 | Harkrider, Jr. |
| 6,350,267 B1 | 2/2002 | Stefanchik |
| 6,350,278 B1 | 2/2002 | Lenker et al. |
| 6,352,503 B1 | 3/2002 | Matsui et al. |
| 6,352,543 B1 | 3/2002 | Cole |
| 6,355,035 B1 | 3/2002 | Manushakian |
| 6,371,956 B1 | 4/2002 | Wilson et al. |
| 6,379,366 B1 | 4/2002 | Fleischman et al. |
| 6,383,195 B1 | 5/2002 | Richard |
| 6,383,197 B1 | 5/2002 | Conlon et al. |
| 6,391,029 B1 | 5/2002 | Hooven et al. |
| 6,402,735 B1 | 6/2002 | Langevin |
| 6,406,440 B1 | 6/2002 | Stefanchik |
| 6,409,733 B1 | 6/2002 | Conlon et al. |
| 6,431,500 B1 | 8/2002 | Jacobs et al. |
| 6,447,511 B1 | 9/2002 | Slater |
| 6,447,523 B1 | 9/2002 | Middleman et al. |
| 6,454,783 B1 | 9/2002 | Piskun |
| 6,454,785 B2 | 9/2002 | De Hoyos Garza |
| 6,464,701 B1 | 10/2002 | Hooven et al. |
| 6,475,104 B1 | 11/2002 | Lutz et al. |
| 6,485,411 B1 | 11/2002 | Konstorum et al. |
| 6,489,745 B1 | 12/2002 | Koreis |
| 6,491,626 B1 | 12/2002 | Stone et al. |
| 6,491,691 B1 | 12/2002 | Morley et al. |
| 6,493,590 B1 | 12/2002 | Wessman et al. |
| 6,494,893 B2 | 12/2002 | Dubrul et al. |
| 6,503,192 B1 | 1/2003 | Ouchi |
| 6,506,190 B1 | 1/2003 | Walshe |
| 6,508,827 B1 | 1/2003 | Manhes |
| 6,543,456 B1 | 4/2003 | Freeman |
| 6,551,270 B1 | 4/2003 | Bimbo et al. |
| 6,554,829 B2 | 4/2003 | Schulze et al. |
| 6,558,384 B2 | 5/2003 | Mayenberger |
| 6,562,035 B1 | 5/2003 | Levin |
| 6,562,052 B2 | 5/2003 | Nobles et al. |
| 6,569,159 B1 | 5/2003 | Edwards et al. |
| 6,572,629 B2 | 6/2003 | Kalloo et al. |
| 6,572,635 B1 | 6/2003 | Bonutti |
| 6,575,988 B2 | 6/2003 | Rousseau |
| 6,579,311 B1 | 6/2003 | Makower |
| 6,585,642 B2 | 7/2003 | Christopher |
| 6,585,717 B1 | 7/2003 | Wittenberger et al. |
| 6,592,559 B1 | 7/2003 | Pakter et al. |
| 6,592,603 B2 | 7/2003 | Lasner |
| 6,602,262 B2 | 8/2003 | Griego et al. |
| 6,605,105 B1 | 8/2003 | Cuschieri et al. |
| 6,610,072 B1 | 8/2003 | Christy et al. |
| 6,610,074 B2 | 8/2003 | Santilli |
| 6,626,919 B1 | 9/2003 | Swanstrom |
| 6,632,229 B1 | 10/2003 | Yamanouchi |
| 6,638,286 B1 | 10/2003 | Burbank et al. |
| 6,652,521 B2 | 11/2003 | Schulze |
| 6,652,551 B1 | 11/2003 | Heiss |
| 6,656,194 B1 | 12/2003 | Gannoe et al. |
| 6,663,641 B1 | 12/2003 | Kovac et al. |
| 6,666,854 B1 | 12/2003 | Lange |
| 6,672,338 B1 | 1/2004 | Esashi et al. |
| 6,673,087 B1 | 1/2004 | Chang et al. |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,699,180 B2 | 3/2004 | Kobayashi |
| 6,699,256 B1 | 3/2004 | Logan et al. |
| 6,699,263 B2 | 3/2004 | Cope |
| 6,708,066 B2 | 3/2004 | Herbst et al. |
| 6,716,226 B2 | 4/2004 | Sixto, Jr. et al. |
| 6,740,030 B2 | 5/2004 | Martone et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,761,685 B2 | 7/2004 | Adams et al. |
| 6,761,718 B2 | 7/2004 | Madsen |
| 6,761,722 B2 | 7/2004 | Cole et al. |
| 6,773,434 B2 | 8/2004 | Ciarrocca |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,864 B2 | 9/2004 | Matsuura et al. |
| 6,790,173 B2 | 9/2004 | Saadat et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,824,548 B2 | 11/2004 | Smith et al. |
| 6,837,847 B2 | 1/2005 | Ewers et al. |
| 6,843,794 B2 | 1/2005 | Sixto, Jr. et al. |
| 6,861,250 B2 | 3/2005 | Cole et al. |
| 6,866,627 B2 | 3/2005 | Nozue |
| 6,878,106 B1 | 4/2005 | Herrmann |
| 6,878,110 B2 | 4/2005 | Yang et al. |
| 6,884,213 B2 | 4/2005 | Raz et al. |
| 6,887,255 B2 | 5/2005 | Shimm |
| 6,896,683 B1 | 5/2005 | Gadberry et al. |
| 6,908,427 B2 | 6/2005 | Fleener et al. |
| 6,908,476 B2 | 6/2005 | Jud et al. |
| 6,916,284 B2 | 7/2005 | Moriyama |
| 6,918,871 B2 | 7/2005 | Schulze |
| 6,926,725 B2 | 8/2005 | Cooke et al. |
| 6,932,810 B2 | 8/2005 | Ryan |

| Patent | Date | Inventor |
|---|---|---|
| 6,932,824 B1 | 8/2005 | Roop et al. |
| 6,932,827 B2 | 8/2005 | Cole |
| 6,932,834 B2 | 8/2005 | Lizardi et al. |
| 6,939,327 B2 | 9/2005 | Hall et al. |
| 6,942,613 B2 | 9/2005 | Ewers et al. |
| 6,945,472 B2 | 9/2005 | Wuttke et al. |
| 6,945,979 B2 | 9/2005 | Kortenbach et al. |
| 6,955,683 B2 | 10/2005 | Bonutti |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,008,375 B2 | 3/2006 | Weisel |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,629 B2 | 8/2006 | Weller et al. |
| 7,087,071 B2 | 8/2006 | Nicholas et al. |
| 7,090,673 B2 | 8/2006 | Dycus et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,703 B2 | 9/2006 | Danitz et al. |
| 7,112,208 B2 | 9/2006 | Morris et al. |
| 7,115,092 B2 | 10/2006 | Park et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,153,321 B2 | 12/2006 | Andrews |
| 7,163,525 B2 | 1/2007 | Franer |
| 7,172,714 B2 | 2/2007 | Jacobson |
| 7,179,254 B2 | 2/2007 | Pendekanti et al. |
| 7,195,612 B2 | 3/2007 | Van Sloten et al. |
| 7,195,631 B2 | 3/2007 | Dumbauld |
| 7,208,005 B2 | 4/2007 | Frecker et al. |
| 7,211,092 B2 | 5/2007 | Hughett |
| 7,223,272 B2 | 5/2007 | Francese et al. |
| 7,232,414 B2 | 6/2007 | Gonzalez |
| 7,232,445 B2 | 6/2007 | Kortenbach et al. |
| 7,241,290 B2 | 7/2007 | Doyle et al. |
| 7,244,228 B2 | 7/2007 | Lubowski |
| 7,252,660 B2 | 8/2007 | Kunz |
| 7,270,663 B2 | 9/2007 | Nakao |
| 7,294,139 B1 | 11/2007 | Gengler |
| 7,301,250 B2 | 11/2007 | Cassel |
| 7,306,597 B2 | 12/2007 | Manzo |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,257 B2 | 2/2008 | Kanehira et al. |
| 7,329,383 B2 | 2/2008 | Stinson |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,393,222 B2 | 7/2008 | Asakura |
| 7,402,162 B2 | 7/2008 | Ouchi |
| 7,404,791 B2 | 7/2008 | Linares et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,257 B2 | 10/2008 | Lashinski et al. |
| 7,452,327 B2 | 11/2008 | Durgin et al. |
| 7,455,208 B2 | 11/2008 | Wales et al. |
| 7,488,295 B2 | 2/2009 | Burbank et al. |
| 7,497,867 B2 | 3/2009 | Lasner et al. |
| 7,507,200 B2 | 3/2009 | Okada |
| 7,524,281 B2 | 4/2009 | Chu et al. |
| 7,524,302 B2 | 4/2009 | Tower |
| 7,534,228 B2 | 5/2009 | Williams |
| 7,544,203 B2 | 6/2009 | Chin et al. |
| 7,548,040 B2 | 6/2009 | Lee et al. |
| 7,549,564 B2 | 6/2009 | Boudreaux |
| 7,553,278 B2 | 6/2009 | Kucklick |
| 7,553,298 B2 | 6/2009 | Hunt et al. |
| 7,559,887 B2 | 7/2009 | Dannan |
| 7,560,006 B2 | 7/2009 | Rakos et al. |
| 7,561,916 B2 | 7/2009 | Hunt et al. |
| 7,566,334 B2 | 7/2009 | Christian et al. |
| 7,575,144 B2 | 8/2009 | Ortiz et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,632,250 B2 | 12/2009 | Smith et al. |
| 7,635,373 B2 | 12/2009 | Ortiz |
| 7,637,903 B2 | 12/2009 | Lentz et al. |
| 7,651,483 B2 | 1/2010 | Byrum et al. |
| 7,651,509 B2 | 1/2010 | Bojarski et al. |
| 7,654,431 B2 | 2/2010 | Hueil et al. |
| 7,662,089 B2 | 2/2010 | Okada et al. |
| 7,666,180 B2 | 2/2010 | Holsten et al. |
| 7,713,270 B2 | 5/2010 | Suzuki |
| 7,736,374 B2 | 6/2010 | Vaughan et al. |
| 7,762,998 B2 | 7/2010 | Birk et al. |
| 7,771,416 B2 | 8/2010 | Spivey et al. |
| 7,780,683 B2 | 8/2010 | Roue et al. |
| 7,794,475 B2 | 9/2010 | Hess et al. |
| 7,837,615 B2 | 11/2010 | Le et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,867,216 B2 | 1/2011 | Wahr et al. |
| 7,896,887 B2 | 3/2011 | Rimbaugh et al. |
| 7,918,869 B2 | 4/2011 | Saadat et al. |
| 7,931,624 B2 | 4/2011 | Smith et al. |
| 7,947,000 B2 | 5/2011 | Vargas et al. |
| 7,955,298 B2 | 6/2011 | Carroll et al. |
| 7,963,975 B2 | 6/2011 | Criscuolo |
| 2001/0049497 A1 | 12/2001 | Kalloo et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |

| Pub. No. | Date | Inventor |
|---|---|---|
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0091391 A1 | 7/2002 | Cole et al. |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0183591 A1 | 12/2002 | Matsuura et al. |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0114732 A1 | 6/2003 | Webler et al. |
| 2003/0120257 A1 | 6/2003 | Houston et al. |
| 2003/0130564 A1 | 7/2003 | Martone et al. |
| 2003/0130656 A1 | 7/2003 | Levin |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0191497 A1 | 10/2003 | Cope |
| 2003/0195565 A1 | 10/2003 | Bonutti |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002735 A1 | 1/2004 | Lizardi et al. |
| 2004/0034369 A1 | 2/2004 | Sauer et al. |
| 2004/0098007 A1 | 5/2004 | Heiss |
| 2004/0101456 A1 | 5/2004 | Kuroshima et al. |
| 2004/0116948 A1 | 6/2004 | Sixto, Jr. et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0210245 A1 | 10/2004 | Erickson et al. |
| 2004/0215058 A1 | 10/2004 | Zirps et al. |
| 2004/0225183 A1 | 11/2004 | Michlitsch et al. |
| 2004/0225186 A1 | 11/2004 | Horne, Jr. et al. |
| 2004/0230095 A1 | 11/2004 | Stefanchik et al. |
| 2004/0230096 A1 | 11/2004 | Stefanchik et al. |
| 2004/0230097 A1 | 11/2004 | Stefanchik et al. |
| 2004/0230161 A1 | 11/2004 | Zeiner |
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2005/0033265 A1 | 2/2005 | Engel et al. |
| 2005/0033277 A1 | 2/2005 | Clague et al. |
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0065397 A1 | 3/2005 | Saadat et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0080413 A1 | 4/2005 | Canady |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0101837 A1 | 5/2005 | Kalloo et al. |
| 2005/0101838 A1 | 5/2005 | Camillocci et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216050 A1 | 9/2005 | Sepetka et al. |
| 2005/0228406 A1 | 10/2005 | Bose |
| 2005/0234297 A1 | 10/2005 | Devierre et al. |
| 2005/0250983 A1 | 11/2005 | Tremaglio et al. |
| 2005/0250990 A1 | 11/2005 | Le et al. |
| 2005/0250993 A1 | 11/2005 | Jaeger |
| 2005/0251166 A1 | 11/2005 | Vaughan et al. |
| 2005/0251176 A1 | 11/2005 | Swanstrom et al. |
| 2005/0261674 A1 | 11/2005 | Nobis et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1 | 2/2006 | Young et al. |
| 2006/0025812 A1 | 2/2006 | Shelton, IV |
| 2006/0025819 A1 | 2/2006 | Nobis et al. |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0058776 A1 | 3/2006 | Bilsbury |
| 2006/0069396 A1 | 3/2006 | Meade et al. |
| 2006/0069424 A1 | 3/2006 | Acosta et al. |
| 2006/0074413 A1 | 4/2006 | Behzadian |
| 2006/0079890 A1 | 4/2006 | Guerra |
| 2006/0089528 A1 | 4/2006 | Tartaglia et al. |
| 2006/0095060 A1 | 5/2006 | Mayenberger et al. |
| 2006/0100687 A1 | 5/2006 | Fahey et al. |
| 2006/0106423 A1 | 5/2006 | Weisel et al. |
| 2006/0111209 A1 | 5/2006 | Hinman et al. |
| 2006/0111210 A1 | 5/2006 | Hinman et al. |
| 2006/0111704 A1 | 5/2006 | Brenneman et al. |
| 2006/0129166 A1 | 6/2006 | Lavelle |

| | | | | | | |
|---|---|---|---|---|---|---|
| 2006/0135962 A1 | 6/2006 | Kick et al. | | 2007/0112385 A1 | 5/2007 | Conlon |
| 2006/0135971 A1 | 6/2006 | Swanstrom et al. | | 2007/0112417 A1 | 5/2007 | Shanley et al. |
| 2006/0135984 A1 | 6/2006 | Kramer et al. | | 2007/0112425 A1 | 5/2007 | Schaller et al. |
| 2006/0142644 A1 | 6/2006 | Mulac et al. | | 2007/0118115 A1 | 5/2007 | Artale et al. |
| 2006/0142652 A1 | 6/2006 | Keenan | | 2007/0123840 A1 | 5/2007 | Cox |
| 2006/0142790 A1 | 6/2006 | Gertner | | 2007/0129605 A1 | 6/2007 | Schaaf |
| 2006/0142798 A1 | 6/2006 | Holman et al. | | 2007/0129719 A1 | 6/2007 | Kendale et al. |
| 2006/0149132 A1 | 7/2006 | Iddan | | 2007/0135709 A1 | 6/2007 | Rioux et al. |
| 2006/0149135 A1 | 7/2006 | Paz | | 2007/0142706 A1 | 6/2007 | Matsui et al. |
| 2006/0161190 A1 | 7/2006 | Gadberry et al. | | 2007/0156127 A1 | 7/2007 | Rioux et al. |
| 2006/0167416 A1 | 7/2006 | Mathis et al. | | 2007/0161855 A1 | 7/2007 | Mikkaichi et al. |
| 2006/0167482 A1 | 7/2006 | Swain et al. | | 2007/0173691 A1 | 7/2007 | Yokoi et al. |
| 2006/0178560 A1 | 8/2006 | Saadat et al. | | 2007/0173869 A1 | 7/2007 | Gannoe et al. |
| 2006/0183975 A1 | 8/2006 | Saadat et al. | | 2007/0173870 A2 | 7/2007 | Zacharias |
| 2006/0184161 A1 | 8/2006 | Maahs et al. | | 2007/0173872 A1 | 7/2007 | Neuenfeldt |
| 2006/0189844 A1 | 8/2006 | Tien | | 2007/0179525 A1 | 8/2007 | Frecker et al. |
| 2006/0189845 A1 | 8/2006 | Maahs et al. | | 2007/0179530 A1 | 8/2007 | Tieu et al. |
| 2006/0190027 A1 | 8/2006 | Downey | | 2007/0197865 A1 | 8/2007 | Miyake et al. |
| 2006/0195084 A1 | 8/2006 | Slater | | 2007/0203487 A1 | 8/2007 | Sugita |
| 2006/0200005 A1 | 9/2006 | Bjork et al. | | 2007/0208364 A1 | 9/2007 | Smith et al. |
| 2006/0200169 A1 | 9/2006 | Sniffin | | 2007/0213754 A1 | 9/2007 | Mikkaichi et al. |
| 2006/0200170 A1 | 9/2006 | Aranyi | | 2007/0225554 A1 | 9/2007 | Maseda et al. |
| 2006/0200199 A1 | 9/2006 | Bonutti et al. | | 2007/0233040 A1 | 10/2007 | Macnamara et al. |
| 2006/0217665 A1 | 9/2006 | Prosek | | 2007/0244358 A1 | 10/2007 | Lee |
| 2006/0217697 A1 | 9/2006 | Lau et al. | | 2007/0250057 A1 | 10/2007 | Nobis et al. |
| 2006/0217742 A1 | 9/2006 | Messerly et al. | | 2007/0255096 A1 | 11/2007 | Stefanchik et al. |
| 2006/0217743 A1 | 9/2006 | Messerly et al. | | 2007/0255100 A1 | 11/2007 | Barlow et al. |
| 2006/0229639 A1 | 10/2006 | Whitfield | | 2007/0255273 A1 | 11/2007 | Fernandez et al. |
| 2006/0229640 A1 | 10/2006 | Whitfield | | 2007/0255303 A1 | 11/2007 | Bakos et al. |
| 2006/0237022 A1 | 10/2006 | Chen et al. | | 2007/0255306 A1 | 11/2007 | Conlon et al. |
| 2006/0237023 A1 | 10/2006 | Cox et al. | | 2007/0260112 A1 | 11/2007 | Rahmani |
| 2006/0241570 A1 | 10/2006 | Wilk | | 2007/0260117 A1 | 11/2007 | Zwolinski et al. |
| 2006/0247576 A1 | 11/2006 | Poncet | | 2007/0260121 A1 | 11/2007 | Bakos et al. |
| 2006/0247673 A1 | 11/2006 | Voegele et al. | | 2007/0260273 A1 | 11/2007 | Cropper et al. |
| 2006/0253004 A1 | 11/2006 | Frisch et al. | | 2007/0270629 A1 | 11/2007 | Charles |
| 2006/0253039 A1 | 11/2006 | McKenna et al. | | 2007/0270889 A1 | 11/2007 | Conlon et al. |
| 2006/0258907 A1 | 11/2006 | Stefanchik et al. | | 2007/0270895 A1 | 11/2007 | Nobis et al. |
| 2006/0258908 A1 | 11/2006 | Stefanchik et al. | | 2007/0270907 A1 | 11/2007 | Stokes et al. |
| 2006/0258910 A1 | 11/2006 | Stefanchik et al. | | 2007/0282371 A1 | 12/2007 | Lee et al. |
| 2006/0258954 A1 | 11/2006 | Timberlake et al. | | 2007/0299387 A1 | 12/2007 | Williams et al. |
| 2006/0258955 A1 | 11/2006 | Hoffman et al. | | 2008/0004650 A1 | 1/2008 | George |
| 2006/0259010 A1 | 11/2006 | Stefanchik et al. | | 2008/0015409 A1 | 1/2008 | Barlow et al. |
| 2006/0264752 A1 | 11/2006 | Rubinsky et al. | | 2008/0015552 A1 | 1/2008 | Doyle et al. |
| 2006/0264904 A1 | 11/2006 | Kerby et al. | | 2008/0027387 A1 | 1/2008 | Grabinsky |
| 2006/0264930 A1 | 11/2006 | Nishimura | | 2008/0033451 A1 | 2/2008 | Rieber et al. |
| 2006/0270902 A1 | 11/2006 | Igarashi et al. | | 2008/0051629 A1 | 2/2008 | Sugiyama et al. |
| 2006/0271102 A1 | 11/2006 | Bosshard et al. | | 2008/0051735 A1 | 2/2008 | Measamer et al. |
| 2006/0276835 A1 | 12/2006 | Uchida | | 2008/0058586 A1 | 3/2008 | Karpiel |
| 2006/0281970 A1 | 12/2006 | Stokes et al. | | 2008/0065169 A1 | 3/2008 | Colliou et al. |
| 2006/0282106 A1 | 12/2006 | Cole et al. | | 2008/0086172 A1 | 4/2008 | Martin et al. |
| 2006/0285732 A1 | 12/2006 | Horn et al. | | 2008/0097472 A1 | 4/2008 | Agmon et al. |
| 2006/0287644 A1 | 12/2006 | Inganas et al. | | 2008/0097483 A1 | 4/2008 | Ortiz et al. |
| 2006/0287666 A1 | 12/2006 | Saadat et al. | | 2008/0103527 A1 | 5/2008 | Martin et al. |
| 2006/0293626 A1 | 12/2006 | Byrum et al. | | 2008/0114384 A1 | 5/2008 | Chang et al. |
| 2007/0002135 A1 | 1/2007 | Glukhovsky | | 2008/0119870 A1 | 5/2008 | Williams |
| 2007/0005019 A1 | 1/2007 | Okishige | | 2008/0125796 A1 | 5/2008 | Graham |
| 2007/0015965 A1 | 1/2007 | Cox et al. | | 2008/0132892 A1 | 6/2008 | Lunsford et al. |
| 2007/0016225 A1 | 1/2007 | Nakao | | 2008/0139882 A1 | 6/2008 | Fujimori |
| 2007/0032700 A1 | 2/2007 | Fowler et al. | | 2008/0147113 A1 | 6/2008 | Nobis et al. |
| 2007/0032701 A1 | 2/2007 | Fowler et al. | | 2008/0171907 A1 | 7/2008 | Long et al. |
| 2007/0043261 A1 | 2/2007 | Watanabe et al. | | 2008/0188868 A1 | 8/2008 | Weitzner et al. |
| 2007/0043345 A1 | 2/2007 | Davalos et al. | | 2008/0200755 A1 | 8/2008 | Bakos |
| 2007/0049800 A1 | 3/2007 | Boulais | | 2008/0200762 A1 | 8/2008 | Stokes et al. |
| 2007/0049902 A1 | 3/2007 | Griffin et al. | | 2008/0200911 A1 | 8/2008 | Long |
| 2007/0051375 A1 | 3/2007 | Milliman | | 2008/0200912 A1 | 8/2008 | Long |
| 2007/0060880 A1 | 3/2007 | Gregorich et al. | | 2008/0200933 A1 | 8/2008 | Bakos et al. |
| 2007/0067017 A1 | 3/2007 | Trapp | | 2008/0200934 A1 | 8/2008 | Fox |
| 2007/0073102 A1 | 3/2007 | Matsuno et al. | | 2008/0208213 A1 | 8/2008 | Benjamin et al. |
| 2007/0073269 A1 | 3/2007 | Becker | | 2008/0221587 A1 | 9/2008 | Schwartz |
| 2007/0079924 A1 | 4/2007 | Saadat et al. | | 2008/0221619 A1 | 9/2008 | Spivey et al. |
| 2007/0088370 A1 | 4/2007 | Kahle et al. | | 2008/0228213 A1 | 9/2008 | Blakeney et al. |
| 2007/0100375 A1 | 5/2007 | Mikkaichi et al. | | 2008/0230972 A1 | 9/2008 | Ganley |
| 2007/0100376 A1 | 5/2007 | Mikkaichi et al. | | 2008/0234696 A1 | 9/2008 | Taylor et al. |
| 2007/0106118 A1 | 5/2007 | Moriyama | | 2008/0243106 A1 | 10/2008 | Coe et al. |
| 2007/0112251 A1 | 5/2007 | Nakhuda | | 2008/0243148 A1 | 10/2008 | Mikkaichi et al. |
| 2007/0112331 A1 | 5/2007 | Weber et al. | | 2008/0243176 A1 | 10/2008 | Weitzner et al. |
| 2007/0112342 A1 | 5/2007 | Pearson et al. | | 2008/0262540 A1 | 10/2008 | Bangera et al. |
| 2007/0112383 A1 | 5/2007 | Conlon et al. | | 2008/0269782 A1 | 10/2008 | Stefanchik et al. |
| 2007/0112384 A1 | 5/2007 | Conlon et al. | | 2008/0269783 A1 | 10/2008 | Griffith |

| | | | | | | |
|---|---|---|---|---|---|---|
| 2008/0275474 A1 | 11/2008 | Martin et al. | | 2010/0191267 A1 | 7/2010 | Fox |
| 2008/0275475 A1 | 11/2008 | Schwemberger et al. | | 2010/0198005 A1 | 8/2010 | Fox |
| 2008/0287737 A1 | 11/2008 | Dejima | | 2010/0198149 A1 | 8/2010 | Fox |
| 2008/0300461 A1 | 12/2008 | Shaw et al. | | 2010/0198244 A1 | 8/2010 | Spivey et al. |
| 2008/0300547 A1 | 12/2008 | Bakos | | 2010/0198248 A1 | 8/2010 | Vakharia |
| 2008/0309758 A1 | 12/2008 | Karasawa et al. | | 2010/0249700 A1 | 9/2010 | Spivey |
| 2008/0312496 A1 | 12/2008 | Zwolinski | | 2010/0286791 A1 | 11/2010 | Goldsmith |
| 2008/0312499 A1 | 12/2008 | Handa et al. | | 2010/0298642 A1 | 11/2010 | Trusty et al. |
| 2008/0312500 A1 | 12/2008 | Asada et al. | | 2010/0312056 A1 | 12/2010 | Galperin et al. |
| 2008/0312506 A1 | 12/2008 | Spivey et al. | | 2010/0331622 A2 | 12/2010 | Conlon |
| 2008/0319436 A1 | 12/2008 | Daniel et al. | | 2010/0331774 A2 | 12/2010 | Spivey |
| 2008/0319439 A1 | 12/2008 | Ootsubu | | 2011/0093009 A1 | 4/2011 | Fox |
| 2009/0054728 A1 | 2/2009 | Trusty | | 2011/0098694 A1 | 4/2011 | Long |
| 2009/0062788 A1 | 3/2009 | Long et al. | | 2011/0098704 A1 | 4/2011 | Long et al. |
| 2009/0062792 A1 | 3/2009 | Vakharia et al. | | 2011/0105850 A1 | 5/2011 | Voegele et al. |
| 2009/0062795 A1 | 3/2009 | Vakharia et al. | | 2011/0112434 A1 | 5/2011 | Ghabrial et al. |
| 2009/0069634 A1 | 3/2009 | Larkin | | 2011/0115891 A1 | 5/2011 | Trusty |
| 2009/0076499 A1 | 3/2009 | Azure | | 2011/0124964 A1 | 5/2011 | Nobis |
| 2009/0082776 A1 | 3/2009 | Cresina | | 2011/0152609 A1 | 6/2011 | Trusty et al. |
| 2009/0082779 A1 | 3/2009 | Nakao | | 2011/0152610 A1 | 6/2011 | Trusty et al. |
| 2009/0112059 A1 | 4/2009 | Nobis | | 2011/0152612 A1 | 6/2011 | Trusty et al. |
| 2009/0112062 A1 | 4/2009 | Bakos | | 2011/0152858 A1 | 6/2011 | Long et al. |
| 2009/0112063 A1 | 4/2009 | Bakos et al. | | 2011/0152859 A1 | 6/2011 | Long et al. |
| 2009/0131751 A1 | 5/2009 | Spivey et al. | | 2011/0152878 A1 | 6/2011 | Trusty et al. |
| 2009/0131932 A1 | 5/2009 | Vakharia et al. | | 2011/0152923 A1 | 6/2011 | Fox |
| 2009/0131933 A1 | 5/2009 | Ghabrial et al. | | 2011/0160514 A1 | 6/2011 | Long et al. |
| 2009/0143639 A1 | 6/2009 | Stark | | | | |
| 2009/0143649 A1 | 6/2009 | Rossi | | FOREIGN PATENT DOCUMENTS | | |
| 2009/0143794 A1 | 6/2009 | Conlon et al. | | DE | 3008120 A1 | 9/1980 |
| 2009/0149710 A1 | 6/2009 | Stefanchik et al. | | DE | 4323585 A1 | 1/1995 |
| 2009/0177031 A1 | 7/2009 | Surti et al. | | DE | 19757056 B4 | 8/2008 |
| 2009/0177219 A1 | 7/2009 | Conlon | | DE | 102006027873 B4 | 10/2009 |
| 2009/0182332 A1 | 7/2009 | Long et al. | | EP | 0086338 A1 | 8/1983 |
| 2009/0192344 A1 | 7/2009 | Bakos et al. | | EP | 0286415 A2 | 10/1988 |
| 2009/0198231 A1 | 8/2009 | Esser et al. | | EP | 0589454 A2 | 3/1994 |
| 2009/0227828 A1 | 9/2009 | Swain et al. | | EP | 0464479 B1 | 3/1995 |
| 2009/0248055 A1 | 10/2009 | Spivey et al. | | EP | 0529675 B1 | 2/1996 |
| 2009/0281559 A1 | 11/2009 | Swain et al. | | EP | 0724863 B1 | 7/1999 |
| 2009/0287236 A1 | 11/2009 | Bakos et al. | | EP | 0760629 B1 | 11/1999 |
| 2009/0292164 A1 | 11/2009 | Yamatani | | EP | 0818974 B1 | 7/2001 |
| 2009/0299135 A1 | 12/2009 | Spivey | | EP | 0947166 B1 | 5/2003 |
| 2009/0299143 A1 | 12/2009 | Conlon et al. | | EP | 0836832 B1 | 12/2003 |
| 2009/0299362 A1 | 12/2009 | Long et al. | | EP | 1402837 A1 | 3/2004 |
| 2009/0299406 A1 | 12/2009 | Swain et al. | | EP | 0744918 B1 | 4/2004 |
| 2009/0299409 A1 | 12/2009 | Coe et al. | | EP | 0931515 B1 | 8/2004 |
| 2009/0306658 A1 | 12/2009 | Nobis et al. | | EP | 1411843 B1 | 10/2004 |
| 2009/0306683 A1 | 12/2009 | Zwolinski et al. | | EP | 1150614 B1 | 11/2004 |
| 2009/0322864 A1 | 12/2009 | Karasawa et al. | | EP | 1477104 A1 | 11/2004 |
| 2009/0326561 A1 | 12/2009 | Carroll, II et al. | | EP | 1481642 A1 | 12/2004 |
| 2010/0010294 A1 | 1/2010 | Conlon et al. | | EP | 1493391 A1 | 1/2005 |
| 2010/0010298 A1 | 1/2010 | Bakos et al. | | EP | 0848598 B1 | 2/2005 |
| 2010/0010299 A1 | 1/2010 | Bakos et al. | | EP | 1281360 B1 | 3/2005 |
| 2010/0010303 A1 | 1/2010 | Bakos | | EP | 1568330 A1 | 8/2005 |
| 2010/0010510 A1 | 1/2010 | Stefanchik | | EP | 1452143 B1 | 9/2005 |
| 2010/0010511 A1 | 1/2010 | Harris et al. | | EP | 1616527 A2 | 1/2006 |
| 2010/0023032 A1 | 1/2010 | Granja Filho | | EP | 1006888 B1 | 3/2006 |
| 2010/0042045 A1 | 2/2010 | Splvey | | EP | 1629764 A1 | 3/2006 |
| 2010/0048990 A1 | 2/2010 | Bakos | | EP | 1013229 B1 | 6/2006 |
| 2010/0049190 A1 | 2/2010 | Long et al. | | EP | 1721561 A1 | 11/2006 |
| 2010/0049223 A1 | 2/2010 | Granja Filho | | EP | 1153578 B1 | 3/2007 |
| 2010/0056861 A1 | 3/2010 | Spivey | | EP | 1334696 B1 | 3/2007 |
| 2010/0056862 A1 | 3/2010 | Bakos | | EP | 1769766 A1 | 4/2007 |
| 2010/0057085 A1 | 3/2010 | Holcomb et al. | | EP | 1836971 A2 | 9/2007 |
| 2010/0057108 A1 | 3/2010 | Spivey et al. | | EP | 1836980 A1 | 9/2007 |
| 2010/0063538 A1 | 3/2010 | Spivey et al. | | EP | 1854421 A2 | 11/2007 |
| 2010/0076451 A1 | 3/2010 | Zwolinski et al. | | EP | 1857061 A1 | 11/2007 |
| 2010/0081877 A1 | 4/2010 | Vakharia | | EP | 1875876 A1 | 1/2008 |
| 2010/0087813 A1 | 4/2010 | Long | | EP | 1891881 A1 | 2/2008 |
| 2010/0113872 A1 | 5/2010 | Asada et al. | | EP | 1902663 A1 | 3/2008 |
| 2010/0121362 A1 | 5/2010 | Clague et al. | | EP | 1477106 B1 | 6/2008 |
| 2010/0130817 A1 | 5/2010 | Conlon | | EP | 1949844 A1 | 7/2008 |
| 2010/0130975 A1 | 5/2010 | Long | | EP | 1518499 B1 | 8/2008 |
| 2010/0131005 A1 | 5/2010 | Conlon | | EP | 1709918 B1 | 10/2008 |
| 2010/0152539 A1 | 6/2010 | Ghabrial et al. | | EP | 1985226 A2 | 10/2008 |
| 2010/0152609 A1 | 6/2010 | Zwolinski et al. | | EP | 1994904 A1 | 11/2008 |
| 2010/0152746 A1 | 6/2010 | Ceniccola et al. | | EP | 1707130 B1 | 12/2008 |
| 2010/0179510 A1 | 7/2010 | Fox et al. | | EP | 1769749 B1 | 11/2009 |
| 2010/0179530 A1 | 7/2010 | Long et al. | | FR | 2731610 A1 | 9/1996 |
| 2010/0191050 A1 | 7/2010 | Zwolinski | | GB | 330629 A | 6/1930 |

| | | | |
|---|---|---|---|
| GB | 2403909 A | 1/2005 | |
| GB | 2421190 A | 6/2006 | |
| GB | 2443261 A | 4/2008 | |
| JP | 56-46674 | 4/1981 | |
| JP | 8-29699 A | 2/1996 | |
| JP | 2002-369791 A | 12/2002 | |
| JP | 2003-088494 A | 3/2003 | |
| JP | 2003-235852 A | 8/2003 | |
| JP | 2004-33525 A | 2/2004 | |
| JP | 2004-065745 A | 3/2004 | |
| JP | 2005-121947 A | 5/2005 | |
| JP | 2005-261514 A | 9/2005 | |
| NL | 1021295 C2 | 2/2004 | |
| SU | 194230 | 5/1967 | |
| SU | 980703 | 12/1982 | |
| WO | WO 84/01707 A1 | 5/1984 | |
| WO | WO 92/13494 A1 | 8/1992 | |
| WO | WO 93/10850 A1 | 6/1993 | |
| WO | WO 93/20760 A1 | 10/1993 | |
| WO | WO 93/20765 A1 | 10/1993 | |
| WO | WO 95/09666 A1 | 4/1995 | |
| WO | WO 96/22056 A1 | 7/1996 | |
| WO | WO 96/27331 A1 | 9/1996 | |
| WO | WO 96/39946 A1 | 12/1996 | |
| WO | WO 97/12557 A1 | 4/1997 | |
| WO | WO 98/01080 A1 | 1/1998 | |
| WO | WO 99/09919 A1 | 3/1999 | |
| WO | WO 99/17661 A1 | 4/1999 | |
| WO | WO 99/30622 A2 | 6/1999 | |
| WO | WO 01/10319 A1 | 2/2001 | |
| WO | WO 01/41627 A2 | 6/2001 | |
| WO | WO 01/58360 A2 | 8/2001 | |
| WO | WO 02/11621 A1 | 2/2002 | |
| WO | WO 02/34122 A2 | 5/2002 | |
| WO | WO 02/094082 A2 | 11/2002 | |
| WO | WO 03/045260 A1 | 6/2003 | |
| WO | WO 03/047684 A2 | 6/2003 | |
| WO | WO 03/059412 A2 | 7/2003 | |
| WO | WO 03/078721 A2 | 9/2003 | |
| WO | WO 03/082129 A2 | 10/2003 | |
| WO | WO 2004/006789 A1 | 1/2004 | |
| WO | WO 2004/028613 A2 | 4/2004 | |
| WO | WO 2004/037123 A1 | 5/2004 | |
| WO | WO 2004/052221 A1 | 6/2004 | |
| WO | WO 2004/086984 A1 | 10/2004 | |
| WO | WO 2005/009211 A2 | 2/2005 | |
| WO | WO 2005/018467 A2 | 3/2005 | |
| WO | WO 2005/037088 A2 | 4/2005 | |
| WO | WO 2005/048827 A1 | 6/2005 | |
| WO | WO 2005/065284 A2 | 7/2005 | |
| WO | WO 2005/097019 A2 | 10/2005 | |
| WO | WO 2005/097234 A2 | 10/2005 | |
| WO | WO 2005/112810 A2 | 12/2005 | |
| WO | WO 2005/120363 A1 | 12/2005 | |
| WO | WO 2006/007399 A1 | 1/2006 | |
| WO | WO 2006/041881 A2 | 4/2006 | |
| WO | WO 2006/060405 A2 | 6/2006 | |
| WO | WO 2006/110733 A2 | 10/2006 | |
| WO | WO 2006/113216 A2 | 10/2006 | |
| WO | WO 2007/014063 A2 | 2/2007 | |
| WO | WO 2007/048085 A2 | 4/2007 | |
| WO | WO 2007/063550 A2 | 6/2007 | |
| WO | WO 2007/100067 A1 | 9/2007 | |
| WO | WO 2007/109171 A2 | 9/2007 | |
| WO | WO 2008/005433 A1 | 1/2008 | |
| WO | WO 2008/041225 A2 | 4/2008 | |
| WO | WO 2008/076337 A1 | 6/2008 | |
| WO | WO 2008/076800 A2 | 6/2008 | |
| WO | WO 2008/101075 A2 | 8/2008 | |
| WO | WO 2008/102154 A2 | 8/2008 | |
| WO | WO 2009/021030 A1 | 2/2009 | |
| WO | WO 2009/027065 A1 | 3/2009 | |
| WO | WO 2009/029065 A1 | 3/2009 | |
| WO | WO 2009/032623 A2 | 3/2009 | |
| WO | WO 2010/088481 A1 | 8/2010 | |

OTHER PUBLICATIONS

Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Endosc., vol. 8, pp. 28-32, 2006.
"Z-Offset Technique Used in the Introduction of Trocar During Laparoscopic Surgery," M.S. Hershey NOTES Presentation to EES NOTES Development Team, Sep. 27, 2007.
F.N. Denans, Nouveau Procede Pour La Guerison Des Plaies Des Intestines. Extrait Des Seances De La Societe Royale De Medecine De Marseille, Pendant Le Mois De Dec. 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).
I. Fraser, "An Historical Perspective on Mechanical Aids in Intestinal Anastamosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastomosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutrues," Dis Col Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.

USGI® EndoSurgical Operating System—g-Prox® Tissue Grasper/Approximation Device; [online] URL: http://www.usgimedical.com/eos/components-gprox.htm—accessed May 30, 2008 (2 pages).

Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.

Endoscopic Retrograde Cholangiopancreatogram (EECP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).

ERCP; Jackson Siegelbaum Gastroenterology; [online] URL: http://www.gicare.com/pated/epdgs20.htm; accessed Feb. 21, 2008 (3 pages).

D.G. Fong et al., "Transcolonic Ventral Wall Hernia Mesh Fixation in a Porcine Model," Endoscopy 2007; 39: 865-869.

B. Rubinsky, Ph.D., "Irreversible Electroporation in Medicine," Technology in Cancer Research and Treatment, vol. 6, No. 4, Aug. 2007, pp. 255-259.

D.B. Nelson, MD et al., "Endoscopic Hemostatic Devices," Gastrointestinal Endoscopy, vol. 54, No. 6, 2001, pp. 833-840.

CRE™ Pulmonary Balloon Dilator; [online] URL: http://www.bostonscientific.com/Device.bsci?page=HCP_Overview&navRelId=1000.1003&method=D..., accessed Jul. 18, 2008 (4 pages).

U.S. Appl. No. 11/744,271, filed May 4, 2007.
U.S. Appl. No. 11/744,279, filed May 4, 2007.
U.S. Appl. No. 11/796,035, filed Apr. 26, 2007.
U.S. Appl. No. 11/796,357, filed Apr. 27, 2007.
U.S. Appl. No. 11/894,358, filed Aug. 21, 2007.
U.S. Appl. No. 11/897,676, filed Aug. 31, 2007.
U.S. Appl. No. 11/968,810, filed Jan. 3, 2008.
U.S. Appl. No. 11/981,070, filed Oct. 31, 2007.
U.S. Appl. No. 11/981,078, filed Oct. 31, 2007.
U.S. Appl. No. 11/981,134, filed Oct. 31, 2007.
U.S. Appl. No. 11/986,084, filed Nov. 20, 2007.
U.S. Appl. No. 11/986,420, filed Nov. 21, 2007.
U.S. Appl. No. 11/986,489, filed Nov. 21, 2007.
U.S. Appl. No. 11/998,370, filed Nov. 29, 2007.
U.S. Appl. No. 12/014,417, filed Jan. 5, 2008.
U.S. Appl. No. 12/019,461, filed Jan. 24, 2008.
U.S. Appl. No. 12/045,318, filed Mar. 10, 2008.
U.S. Appl. No. 12/109,673, filed Apr. 25, 2008.
U.S. Appl. No. 12/109,699, filed Apr. 25, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/202,740, filed Sep. 2, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 11/762,855, filed Jun. 14, 2007.
U.S. Appl. No. 12/192,372, filed Aug. 15, 2008.
U.S. Appl. No. 12/203,330, filed Sep. 3, 2008.
U.S. Appl. No. 12/197,749, filed Aug. 25, 2008.
U.S. Appl. No. 12/197,653, filed Aug. 25, 2008.
U.S. Appl. No. 12/203,458, filed Sep. 3, 2008.
U.S. Appl. No. 12/201,812, filed Aug. 29, 2008.
U.S. Appl. No. 12/207,306, filed Sep. 9, 2008.
U.S. Appl. No. 12/243,334, filed Oct. 1, 2008.
U.S. Appl. No. 12/234,425, filed Sep. 19, 2008.
U.S. Appl. No. 11/756,914, filed Jun. 1, 2007.

U.S. Appl. No. 12/060,601, filed Apr. 1, 2008.

International Search Report and Written Opinion for PCT/US2009/045580, Aug. 21, 2009 (14 pages).

J.D. Paulson, M.D., et al., "Development of Flexible Culdoscopy," The Journal of the American Association of Gynecologic Laparoscopists, Nov. 1999, vol. 6, No. 4, pp. 487-490.

H. Seifert, et al., "Retroperitoneal Endoscopic Debridement for Infected Peripancreatic Necrosis," The Lancet, Research Letters, vol. 356, Aug. 19, 2000, pp. 653-655.

K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Oct. 3, 1997; Accepted Mar. 31, 1998).

D. Wilhelm et al., "An Innovative, Safe and Sterile Sigmoid Access (ISSA) for NOTES," Endoscopy 2007, vol. 39, pp. 401-406.

Nakazawa et al., "Radiofrequency Ablation of Hepatocellular Carcinoma: Correlation Between Local Tumor Progression After Ablation and Ablative Margin," AJR, 188, pp. 480-488 (Feb. 2007).

Miklavčič et al., "A validated model of in vivo electric field distribution in tissues for electrochemotherapy and for DNA electrotransfer for gene therapy," Biochimica et Biophysica Acta, 1523, pp. 73-83 (2000).

Evans, "Ablative and cathether-delivered therapies for colorectal liver metastases (CRLM)," EJSO, 33, pp. S64-S75 (2007).

Wong et al., "Combined Percutaneous Radiofrequency Ablation and Ethanol Injection for Hepatocellular Carcinoma in High-Risk Locations," AJR, 190, pp. W187-W195 (2008).

Heller et al., "Electrically mediated plasmid DNA delivery to hepatocellular carcinomas in vivo," Gene Therapy, 7, pp. 826-829 (2000).

Widera et al., "Increased DNA Vaccine Delivery and Immunogenicity by Electroporation In Vivo," The Journal of Immunology, 164, pp. 4635-4640 (2000).

Weaver et al., "Theory of electroporation: A review," Bioelectrochemistry and Bioenergetics, 41, pp. 135-160 (1996).

Mulier et al., "Radiofrequency Ablation Versus Resection for Resectable Colorectal Liver Metastases: Time for a Randomized Trial?" Annals of Surgical Oncology, 15(1), pp. 144-157 (2008).

Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).

Guyton et al., "Membrane Potentials and Action Potentials," W.B. Sanders, ed. Textbook of Medical Physiology, p. 56 (2000).

Guyton et al., "Contraction of Skeletal Muscle," Textbook of Medical Physiology, pp. 82-84 (2000).

"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).

"Ethicon Endo-Surgery Studies Presented At DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).

Castellvi et al., "Hybrid Transvaginal NOTES Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).

Castellvi et al., "Hybrid Transvaginal NOTES Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).

U.S. Appl. No. 12/130,010, filed May 30, 2008.
U.S. Appl. No. 12/277,975, filed Nov. 25, 2008.
U.S. Appl. No. 12/277,957, filed Nov. 25, 2008.
U.S. Appl. No. 12/332,938, filed Dec. 11, 2008.
U.S. Appl. No. 12/337,340, filed Dec. 17, 2008.
U.S. Appl. No. 12/352,451, filed Jan. 12, 2009.
U.S. Appl. No. 12/359,824, filed Jan. 26, 2009.
U.S. Appl. No. 12/352,375, filed Jan. 12, 2009.
U.S. Appl. No. 12/359,053, filed Jan. 23, 2009.
U.S. Appl. No. 12/362,826, filed Jan. 30, 2009.
U.S. Appl. No. 12/363,137, filed Jan. 30, 2009.

U.S. Appl. No. 12/364,172, filed Feb. 2, 2009.
U.S. Appl. No. 12/364,256, filed Feb. 2, 2009.
U.S. Appl. No. 12/413,479, filed Mar. 27, 2009.
U.S. Appl. No. 12/468,462, filed May 19, 2009.
U.S. Appl. No. 12/607,252, filed Oct. 28, 2009.
U.S. Appl. No. 12/580,400, filed Oct. 16, 2009.
U.S. Appl. No. 12/607,388, filed Oct. 28, 2009.
U.S. Appl. No. 12/612,911, filed Nov. 5, 2009.
U.S. Appl. No. 12/614,143, filed Nov. 6, 2009.
U.S. Appl. No. 12/617,998, filed Nov. 13, 2009.
OCTO Port Modular Laparoscopy System for Single Incision Access, Jan. 4, 2010; URL http://www.medgadget.com/archives/2010/01/octo_port_modular_laparo...; accessed Jan. 5, 2010 (4 pages).
Hakko Retractors, obtained Aug. 25, 2009 (5 pages).
U.S. Appl. No. 12/640,440, filed Dec. 17, 2009.
U.S. Appl. No. 12/640,469, filed Dec. 17, 2009.
U.S. Appl. No. 12/640,476, filed Dec. 17, 2009.
U.S. Appl. No. 12/640,492, filed Dec. 17, 2009.
U.S. Appl. No. 12/641,823, filed Dec. 18, 2009.
U.S. Appl. No. 12/641,853, filed Dec. 18, 2009.
U.S. Appl. No. 12/641,837, filed Dec. 18, 2009.
U.S. Appl. No. 12/651,181, filed Dec. 31, 2009.
U.S. Appl. No. 12/696,598, filed Jan. 29, 2010.
U.S. Appl. No. 12/696,626, filed Jan. 29, 2010.
U.S. Appl. No. 12/752,701, filed Apr. 1, 2010.
Zadno et al., "Linear Superelasticity in Cold-Worked NI-TI," Engineering Aspects of Shape Memory Alloys, pp. 414-419 (1990).
U.S. Appl. No. 13/013,131, filed Jan. 25, 2011.
U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.
International Preliminary Report on Patentability for PCT/US2009/045580, Nov. 30, 2010 (7 pages).

* cited by examiner ure configuration.
SURGICAL FASTENING DEVICE

BACKGROUND

Various embodiments relate to surgical fastening devices and to creating and/or placing surgical fastening devices. The surgical fastening devices may be particularly suited to use in open, laparoscopic and/or endoscopic surgical environments and, in various embodiments, may be inserted through a natural orifice in the body to reach a surgical site.

Surgical clips are generally used to apply clamping force to ducts, vessels, and other tissues. In addition, surgical clips are used to control bleeding of a tissue in lieu of suturing or stapling where suturing and stapling are difficult, such as in laparoscopic and/or endoscopic surgical environments. For example, surgical clips may be used to close perforations in the gastrointestinal tract resulting from ulcers, polypectomies, etc. Because of their relatively large size, it is difficult to place multiple surgical clips in close proximity to one another. Therefore, if a surgeon fails to place a surgical clip at an optimum location on the first attempt, it may be necessary to remove the surgical clip before placing another. This may unnecessarily lengthen surgical procedures and cause damage to tissue.

It is also known to use surgical sutures to close various wounds. In a laparoscopic or endoscopic environment, however, it may be difficult to pass instruments suitable for performing a typical "pass and catch" suturing method through a trocar or an endoscope working channel. Accordingly, various suture anchors such as "T-tags" and other fasteners have been developed. These fasteners anchor themselves either through or within tissue. Suture material is then secured to the anchors, allowing a wound or other opening to be closed. Suture anchors, however, present their own difficulties. For example, placing a suture anchor often requires partially or completely perforating the tissue, creating a risk of puncture or injury to surrounding tissue and organs. Also, once a suture anchor has been placed, it may be difficult to remove it or place additional anchors in close proximity. Additional fastening methods are needed.

FIGURES

The novel features of the various embodiments are set forth with particularity in the appended claims. The various embodiments, however, both as to organization and methods of operation, together with advantages thereof, may best be understood by reference to the following description, taken in conjunction with the accompanying drawings as follows.

DESCRIPTION

Various embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting embodiments and that the scope of the various embodiments is defined solely by the claims. The features illustrated or described in connection with one embodiment may be combined with the features of other embodiments. Such modifications and variations are intended to be included within the scope of the claims.

It will be appreciated that the terms "proximal" and "distal" are used herein with reference to a clinician manipulating an end of an instrument extending from the clinician to a surgical site (e.g., through a trocar, through a natural orifice, through an open surgical site, etc.). The term "proximal" refers to the portion closest to the clinician, and the term "distal" refers to the portion located away from the surgeon. It will be further appreciated that for conciseness and clarity, spatial terms such as "vertical," "horizontal," "up," and "down" may be used herein with respect to the drawings. However, surgical instruments are used in many orientations and positions, and these terms are not intended to be limiting and absolute.

Figure 1:
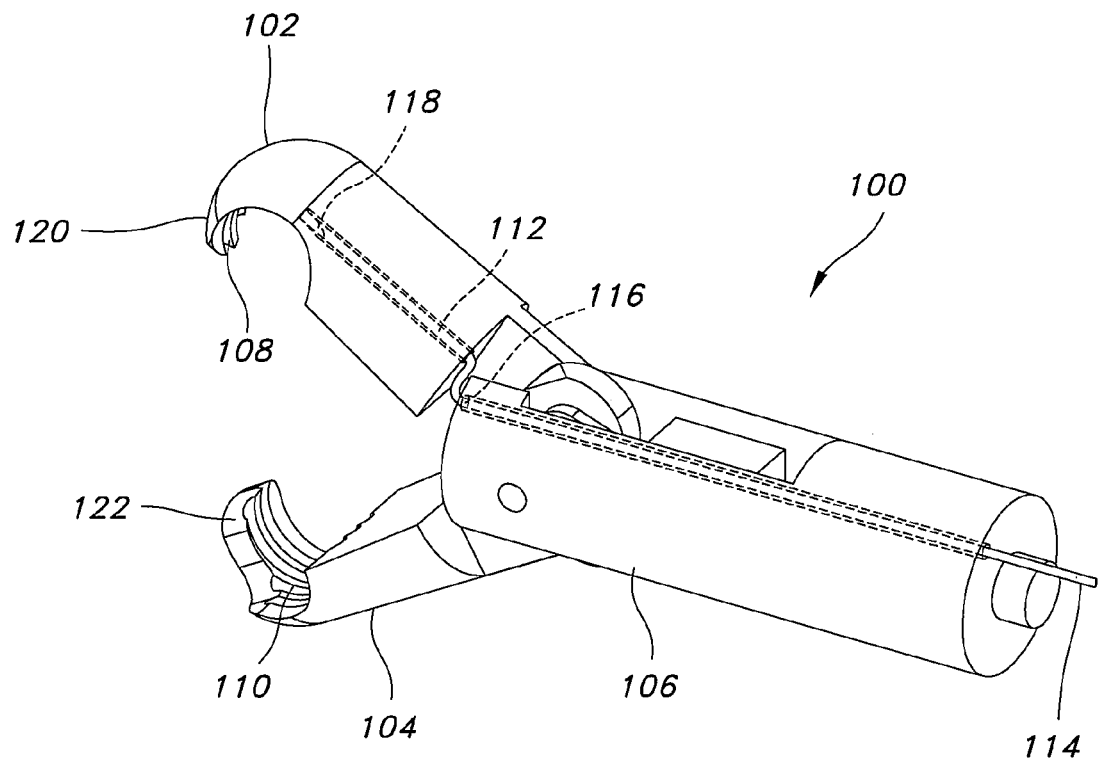
FIG. 1 illustrates one embodiment of an end effector of a surgical device for creating and placing helical surgical fasteners in an open position.

The various embodiments generally provide methods and devices for creating and placing helical surgical fasteners. FIG. 1 illustrates one embodiment of an end effector 100 of a surgical device for creating and placing helical surgical fasteners. In FIG. 1, the end effector 100 is shown in an open position. The end effector 100 may be utilized with any suitable surgical device type and may be introduced to a surgical site according to any suitable method. For example, the end effector 100 may be utilized in a traditional open surgical environment, or may be introduced via a trocar in a laparoscopic surgical environment. According to various embodiments, the end effector 100 may be introduced via natural orifices and may be combined with trans-organ techniques. In one embodiment, Natural Orifice Translumenal Endoscopic Surgery (NOTES)™ techniques may be employed to introduce instruments into the patient and carry out the various procedures described hereinbelow. A NOTES™ technique is a minimally invasive therapeutic procedure that may be employed to treat diseased tissue through a natural opening of the patient without making incisions in the abdomen. A natural opening may be the mouth, anus, and/or vagina. Medical implantable instruments may be introduced into the patient to the target area via the natural opening. In a NOTES™ technique, a surgeon inserts a flexible endoscope into one or more natural openings of the patient to view the target area using a camera. During endoscopic surgery the surgeon inserts surgical devices through one or more lumens or working channels of the endoscope to perform various key surgical activities (KSA). These KSAs include forming an anastomosis between organs, repairing ulcers and other wounds, etc.

Figure 2:
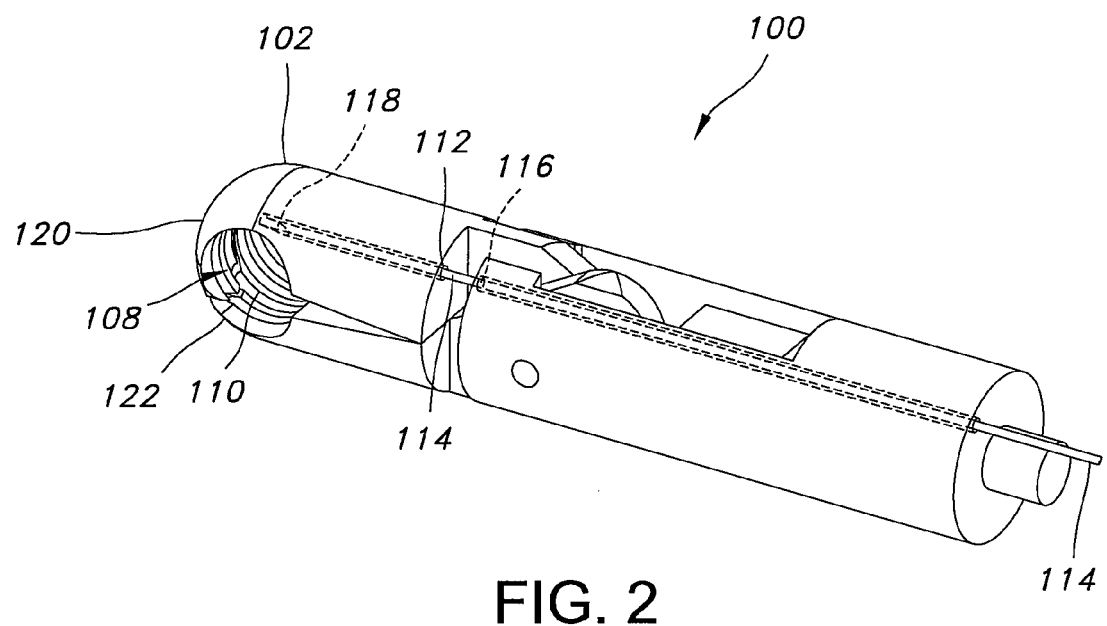
FIG. 2 illustrates one embodiment of the end effector of FIG. 1 in a closed position.

Referring again to FIG. 1, the end effector 100 may comprise a first jaw member 102 and a second jaw member 104 pivotably connected to a housing or clevis 106. At least one of the jaw members 102, 104 may be pivotable relative to the other to transition the end effector 100 from the open position shown in FIG. 1 to a closed position. FIG. 2 shows one embodiment of the end effector 100 in a closed position. The jaw members 102, 104 may each define grooves 108, 110. When the jaw members 102, 104 are moved to the closed position, the grooves 108, 110 may come together to form a combined groove 108, 110 that may be helical or about helical. According to various embodiments, the jaw members 102, 104 may comprise interlocking teeth. FIGS. 1 and 2 illustrate a pair of interlocking teeth 120, 122, however, additional teeth may be provided. The teeth 120, 122 may serve to grab and grip tissue when the end effector 100 is in the closed position. As shown in FIGS. 1 and 2, the grooves 108, 110 are positioned at distal portions of the respective jaw members 102, 104.

Jaw member 102 may additionally define a wire opening 112. The wire opening 112 may extend distally through the jaw member 102 and may align with the groove 108 (e.g., an end of the groove). A corresponding wire opening 116 may extend proximally through the clevis 106 and may ultimately extend to a handle (not shown in FIG. 2) or another clinician-accessible location. In this way, a wire 114 may be extended from the clinician-accessible location, through the clevis 106, through the jaw member 102 and ultimately to the grooves 108, 110 to create and place a helical fastener, as described herein. The wire 114 may be any wire suitably sized and constituted to form helical fasteners. According to various embodiments, the wire 114 may be between 5 and 15 thousandths of an inch. The wire 114 may be made from any suitable material including, for example, stainless steel, titanium, cobalt chrome, etc.

Figure 3:
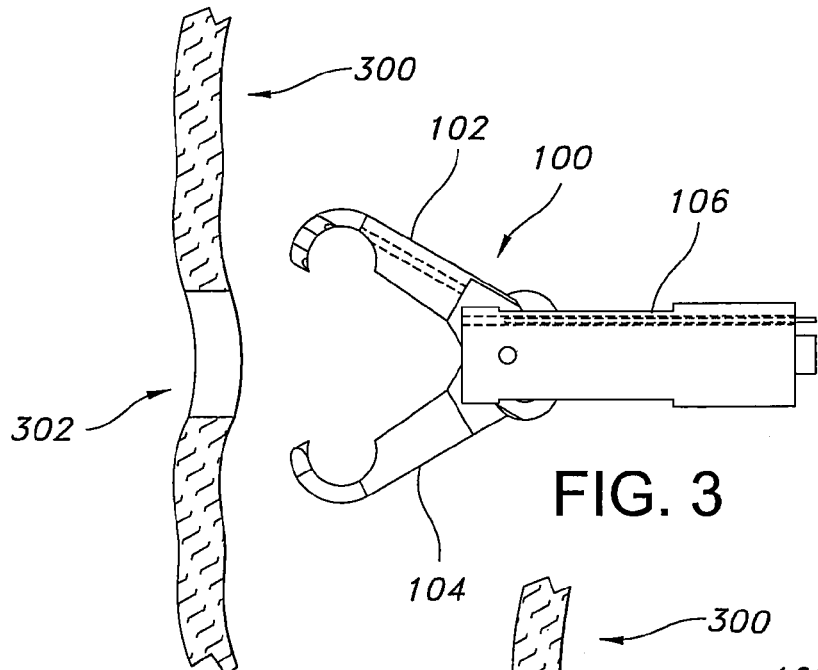
FIG. 3 illustrates one embodiment of the end effector of FIG. 1 approaching tissue.
Figure 4:
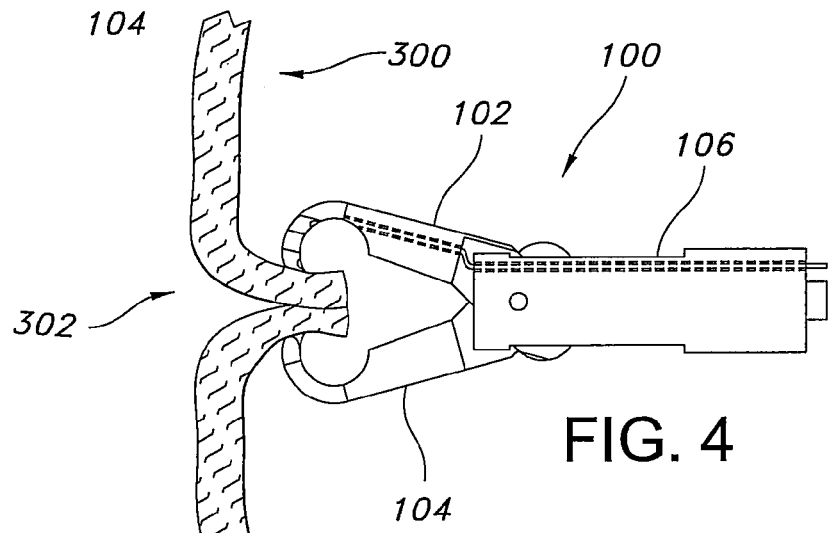
FIG. 4 illustrates one embodiment of the end effector of FIG. 1 with tissue placed between jaw members and the jaw members in the closed position.
Figure 5:
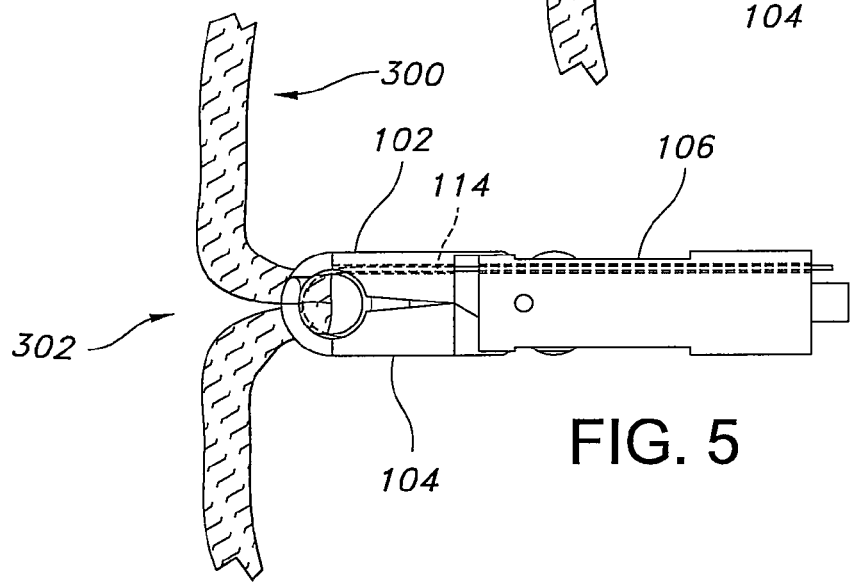
FIG. 5 illustrates one embodiment of the end effector of FIG. 1 with a wire advancing through a wire opening of a jaw member.

According to various embodiments, the end effector 100 may apply helical fasteners by grasping tissue, and then forming the wire 114 into a helical shape utilizing the grooves 108, 110. Because tissue is present between the jaw members 102, 104 while the wire 114 is formed into a helical shape, the wire may be forced through the tissue, which may tend to bind the tissue. FIG. 3 illustrates one embodiment of the end effector 100 approaching tissue 300. The tissue 300 may have an opening 302 to be closed by a helical fastener, as described herein. The opening 302 may be any naturally or artificially occurring opening in tissue 300 including, for example, an incision, an ulcer or other wound, or part of an anastomosis. FIG. 4 illustrates one embodiment of the end effector 100 with the tissue 300 placed between the jaw members 102, 104, which are shown in the closed position. Force provided by the jaw members 102, 104 may tend to close the opening 302, as shown. FIG. 5 illustrates one embodiment of the end effector 100 with wire 114 advancing through the wire opening 112 of the jaw member 102. As the wire 114 advances through the wire opening 112, it may encounter the grooves 108, 110, which may tend to form the wire into a helical or near-helical shape. Because the tissue 300 is present within the jaw members 102, 104, the helical or near-helical shape may be formed through the tissue 300. As a result, the helical shaped wire 114 may serve as a fastener and, if desired, may be placed to bind the opening 302.

Figure 6:
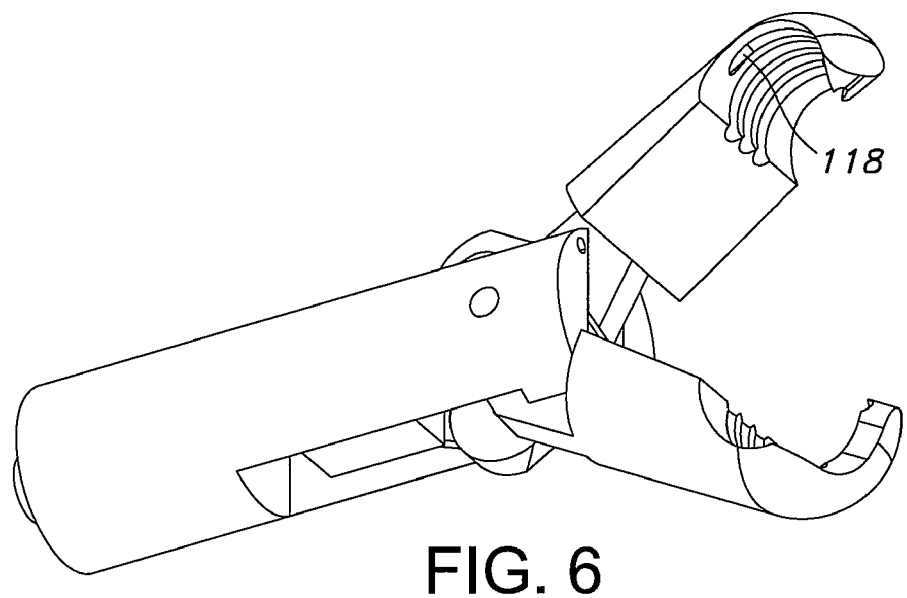
FIG. 6 illustrates one embodiment of the end effector of FIG. 1 with the jaw members in an open position showing a beveled edge at a distal end of the wire opening.
Figure 7:
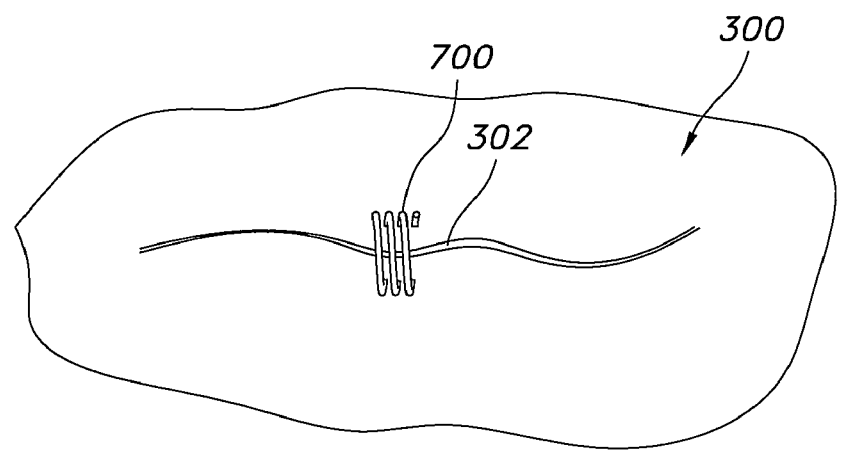
FIG. 7 illustrates one embodiment of the tissue after the end effector of FIG. 1 has been opened and removed.

When the wire 114 reaches the end of the grooves 108, 110 and/or when the clinician determines that the resulting helical fastener is of sufficient width, the clinician may sever the fastener from the remainder of the wire 114 in any suitable way. For example, FIG. 6 illustrates one embodiment of the end effector 100 with the jaw members 102, 104 in an open position showing a beveled edge 118 at a distal end of the wire opening 112. When the wire 114 is to be cut, it may be retracted through the opening 112. When the wire 114 is substantially parallel to the wire opening 112, it may pass smoothly through. When a curved portion of the wire 114 contacts the beveled edge 118, however, the beveled edge 118 may sever the wire 114, leaving the helical-shaped portion of the wire 114 embedded in the tissue 300 as a fastener. The end effector 100 may then be opened and removed from the surgical site. FIG. 7 illustrates one embodiment of the tissue 300 after the end effector 100 has been opened and removed. The fastener 700, formed from the wire 114, may bind the previous opening 302. In other embodiments, the wire 114 may be severed according to other methods. For example, cutters (not shown) may be provided to the surgical site to cut the wire 114 (e.g., via an endoscope working channel, trocar, etc.).

Figure 8:
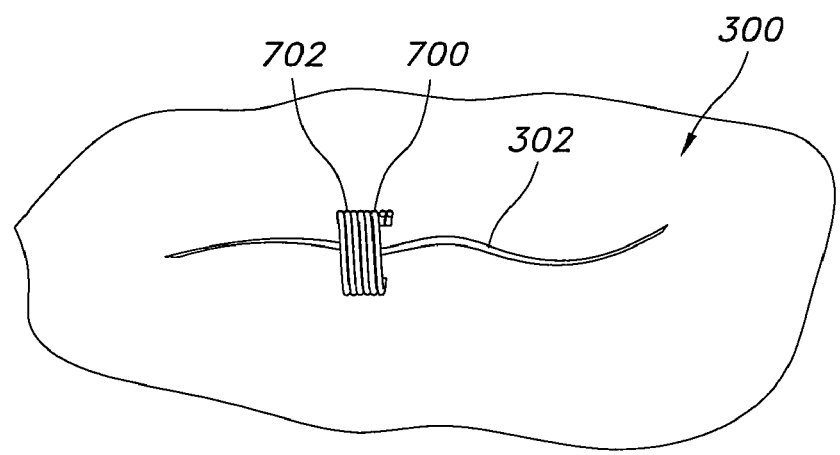
FIG. 8 illustrates one embodiment of the tissue with an additional fastener placed.

According to various embodiments, it may be necessary and/or desirable to place additional helical fasteners. For example, the opening 302 may be a bleeding ulcer or other bleeding wound, making it difficult for the clinician to know exactly where a fastener should be placed. Also, the size of the opening 302 may require additional fasteners. Because of the substantially helical shape of the fastener 700, it may be possible for a clinician to place a second fastener very close to the first fastener 700. FIG. 8 illustrates one embodiment of the tissue 300 with an additional fastener 702 placed. As illustrated, the second fastener 702 is interlaced within the first fastener 700. By contrast, if a surgical clip or suture anchor is slightly misplaced, it may not be possible to place another close by. Instead, the clinician may have to remove the errant clip or anchor, which may cause additional damage to the tissue.

Figure 9:
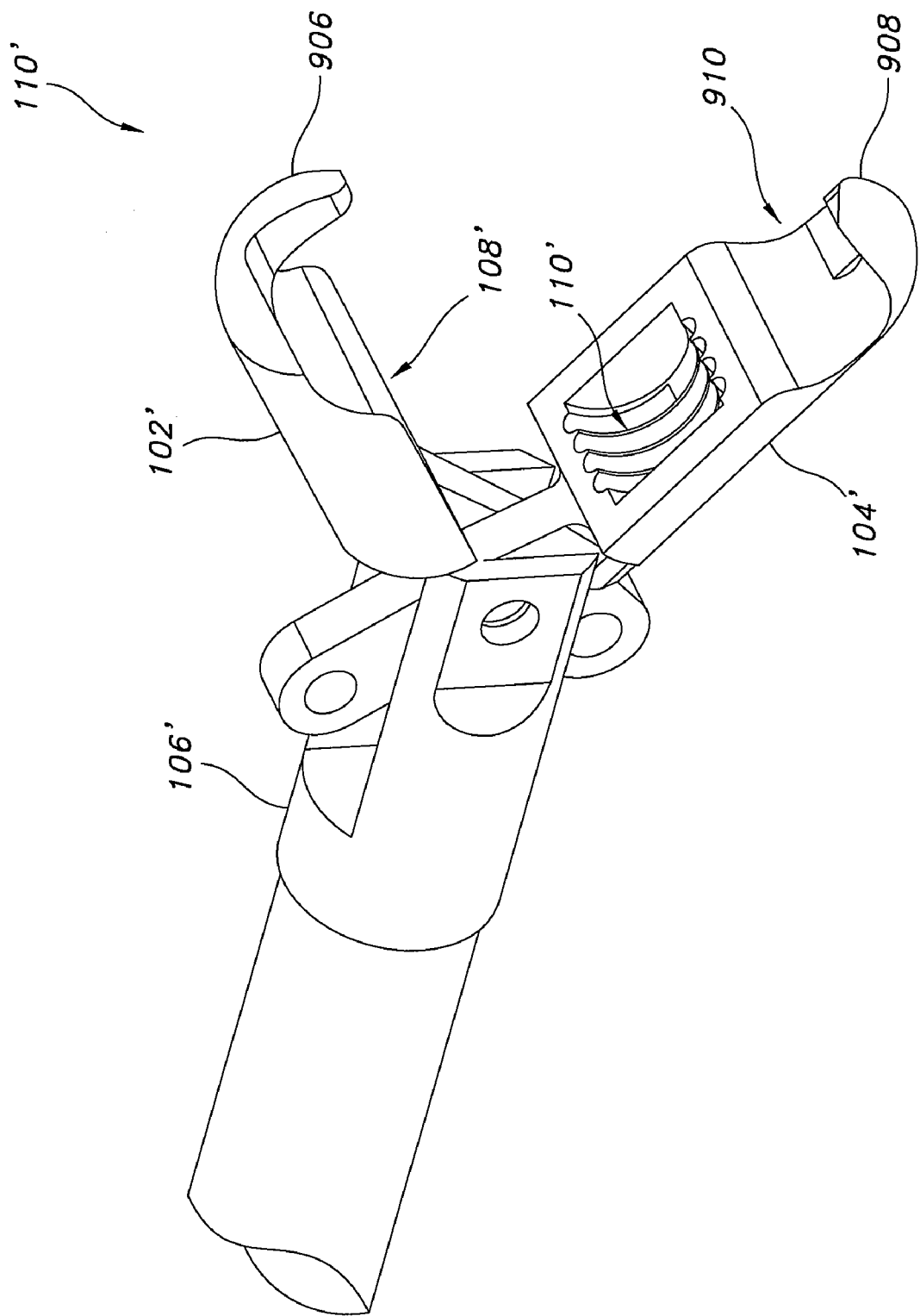
FIG. 9 illustrates one embodiment of an end effector with an alternate groove configuration.

FIG. 9 illustrates one embodiment of an end effector 100' with an alternate groove configuration. The end effector 100' may comprise first and second jaw members 102', 104'. The jaw members 102', 104' may comprise grooves 108', 110' and two or more interlocking teeth 906, 908. In contrast to the embodiments shown in FIGS. 1-8, the grooves 108', 110' may be positioned proximally relative to the teeth 906, 908. In use, the teeth 906, 908 may be used to grasp tissue and pull it towards the grooves 108', 110', where it may be compressed when the end effector 100' is closed. The end effector 100' may also define a wire opening (not shown in FIG. 9) in line with at least one of the grooves 108', 110'. A wire (not shown in FIG. 9) may be advanced through the wire opening and grooves 108', 110' to form a helical wire portion that may serve as a helical fastener, for example, as described above.

Figure 10:
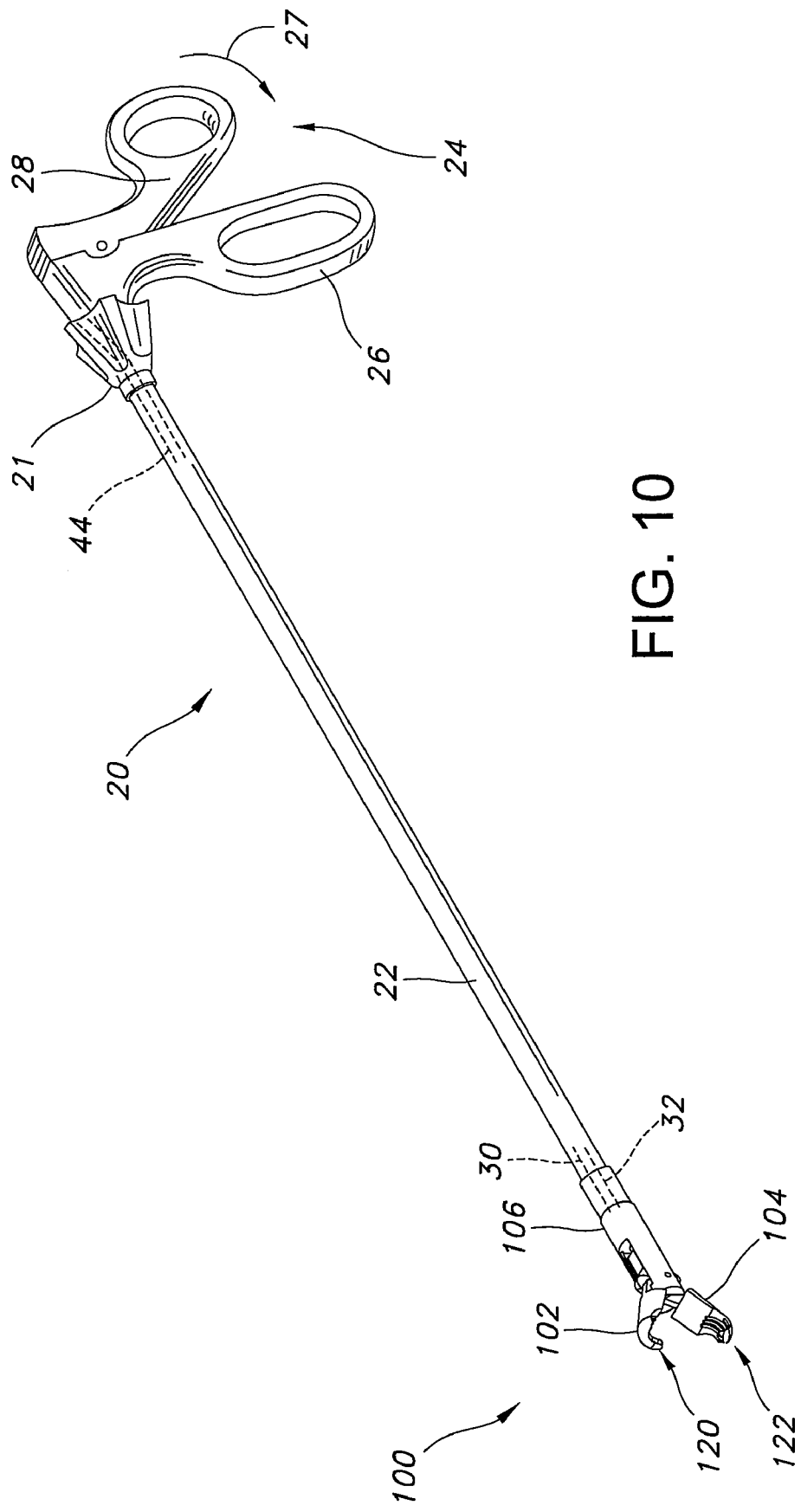
FIG. 10 illustrates one embodiment of a surgical instrument that may utilize the end effector of FIG. 1 showing a hand piece and shaft assembly.
Figure 11:
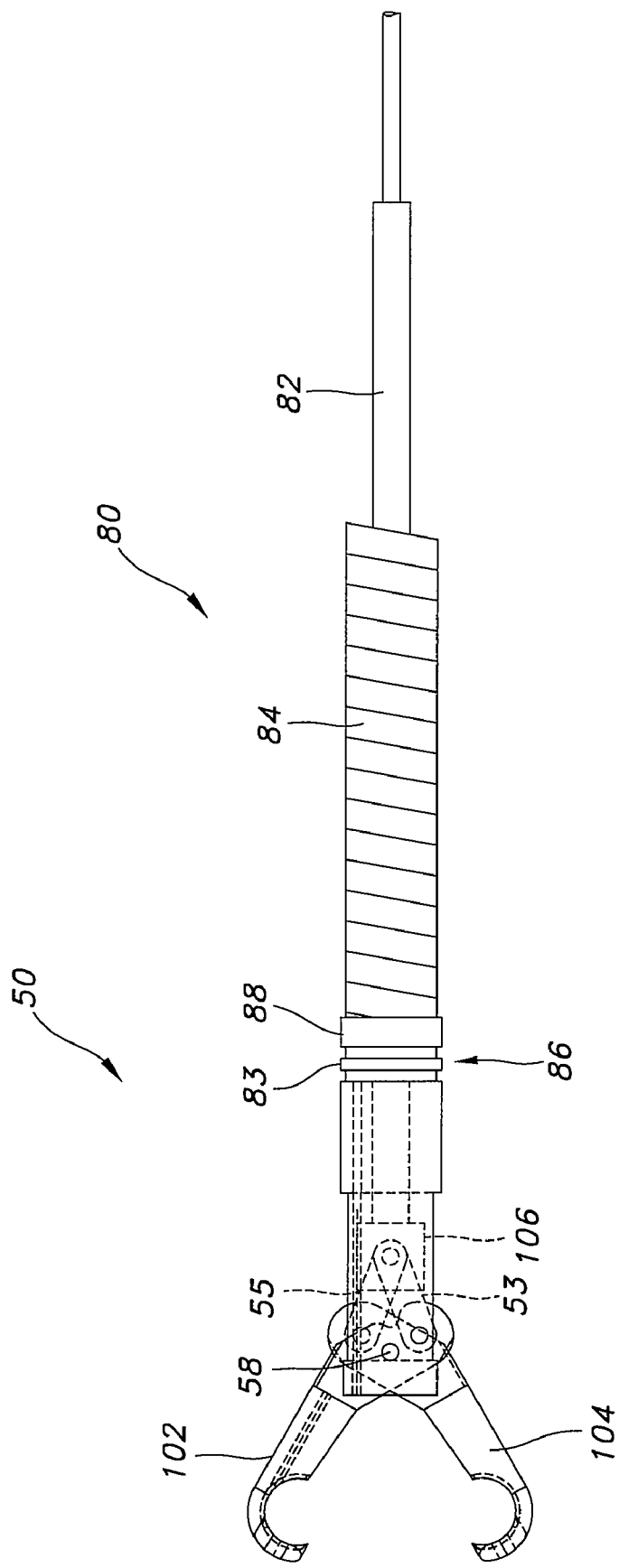
FIG. 11 is an elevational view of one embodiment of an end effector and a shaft assembly of a surgical instrument.
Figure 12:
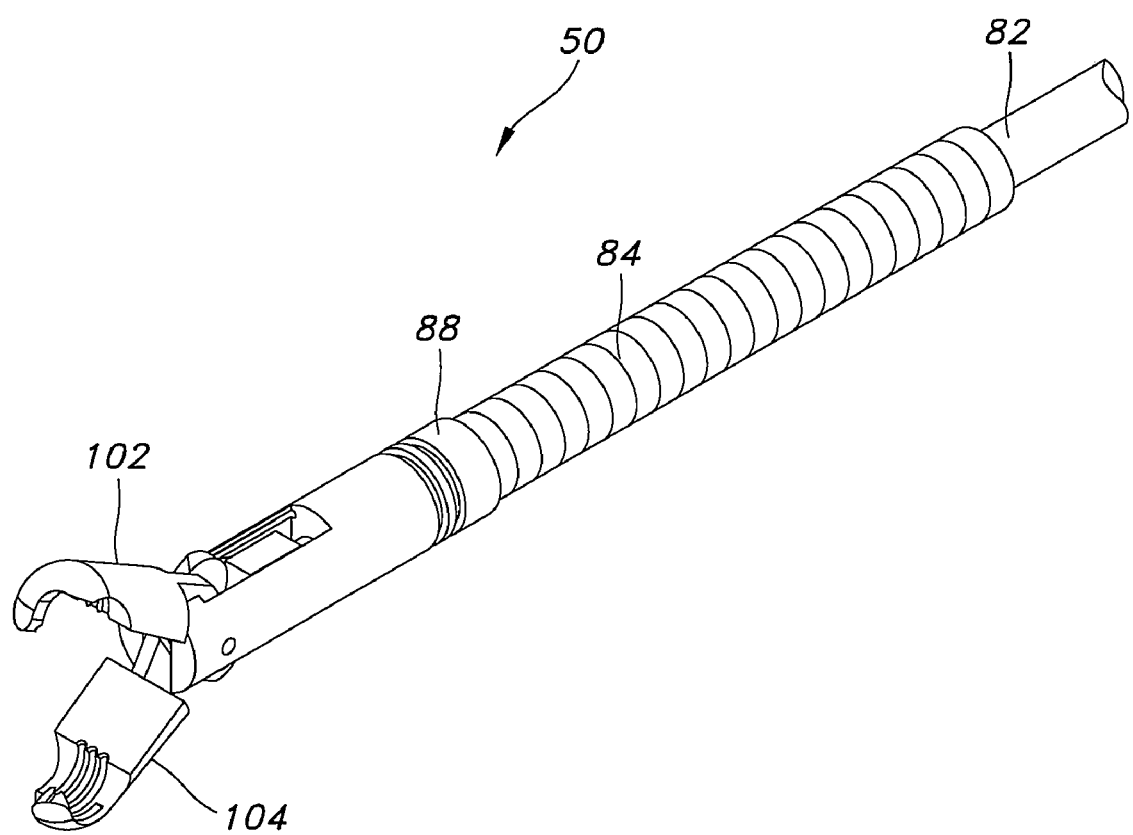
FIG. 12 is a perspective view of one embodiment of the end effector of FIG. 11.
Figure 13:
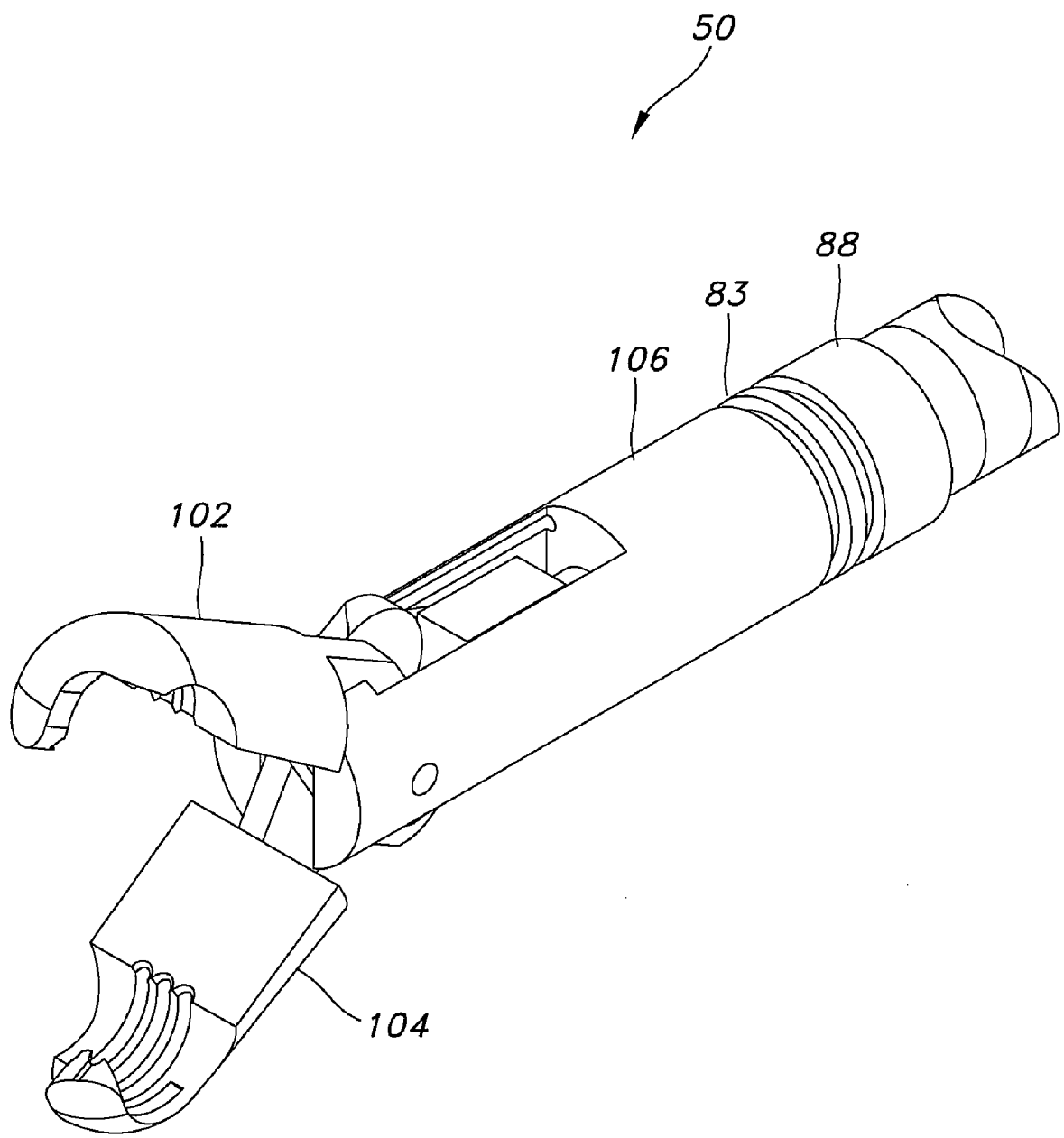
FIG. 13 is an additional perspective view of one embodiment of the end effector of FIG. 11.
Figure 14:
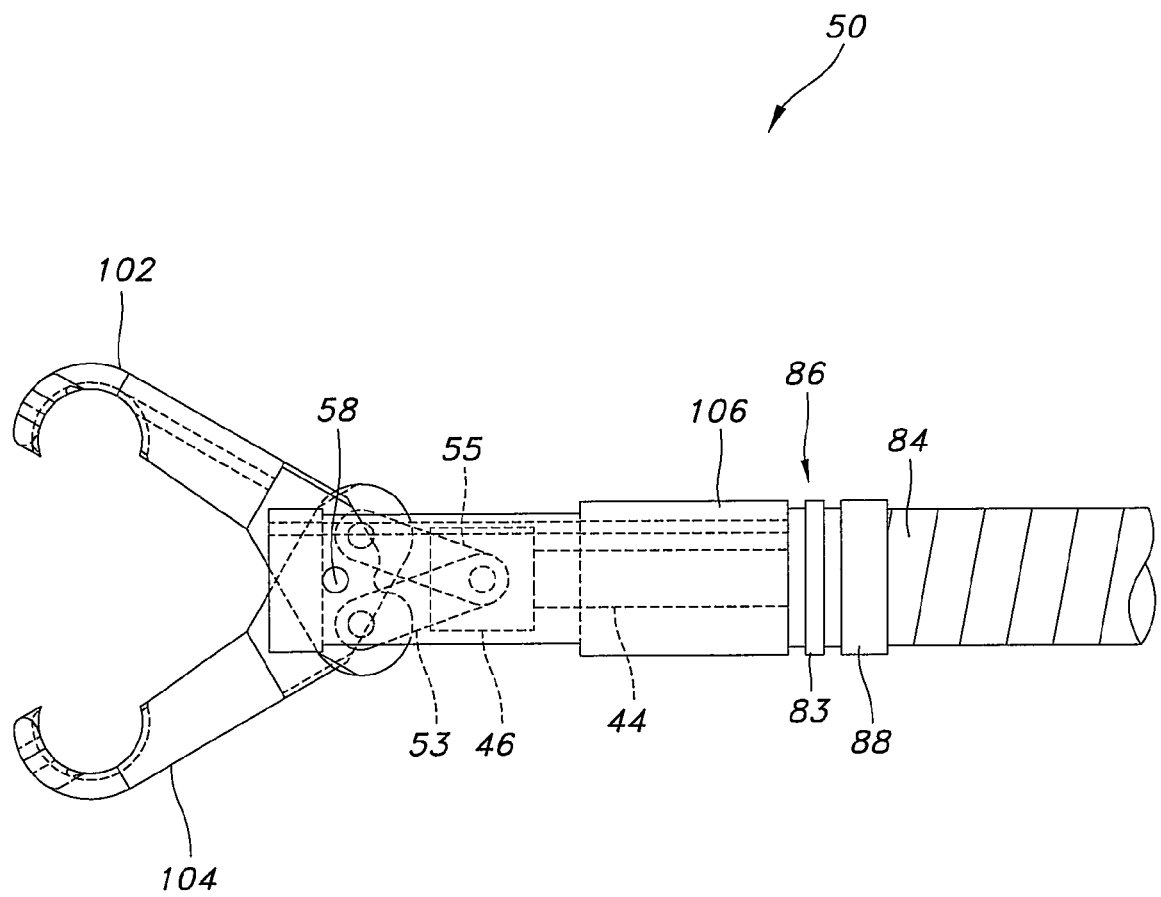
FIG. 14 is a left elevational view of one embodiment of the end effector of FIG. 11.
Figure 15:
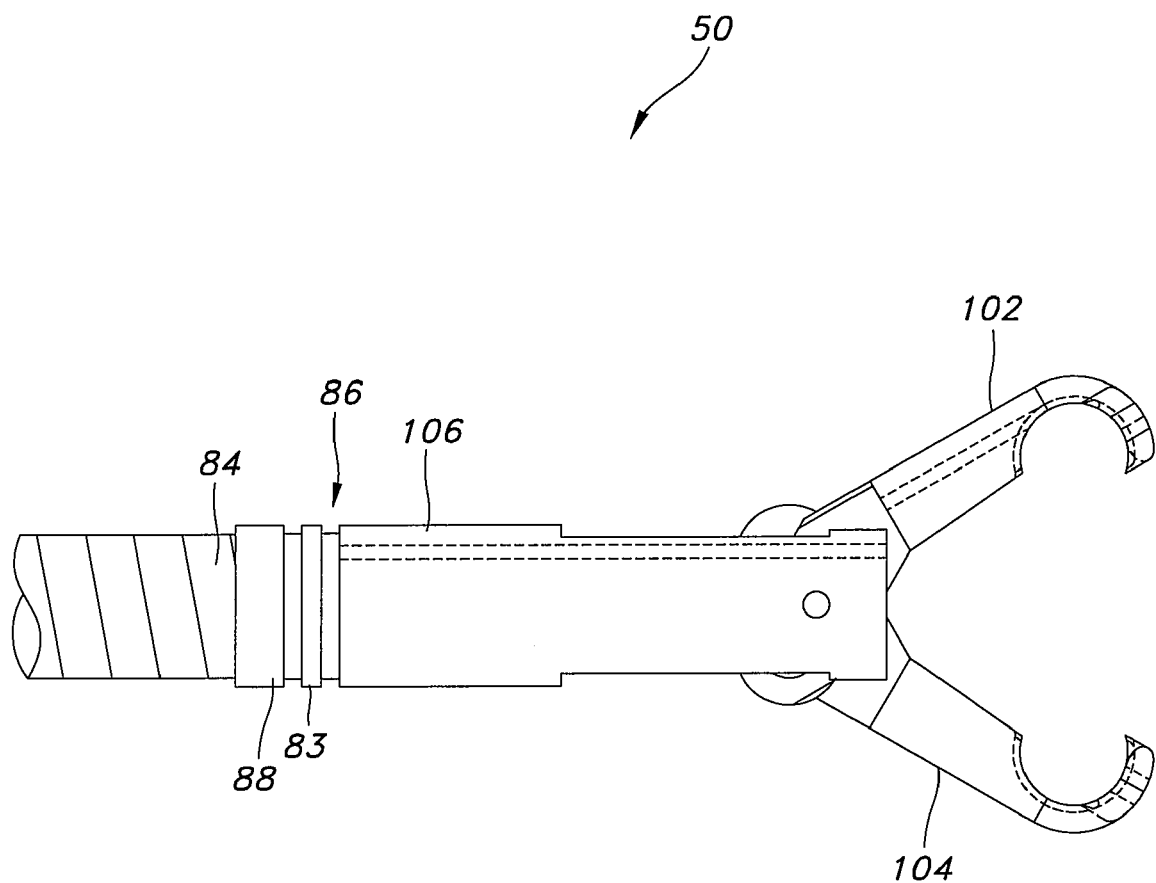
FIG. 15 is a right elevational view of one embodiment of the end effector of FIG. 11.
Figure 16:
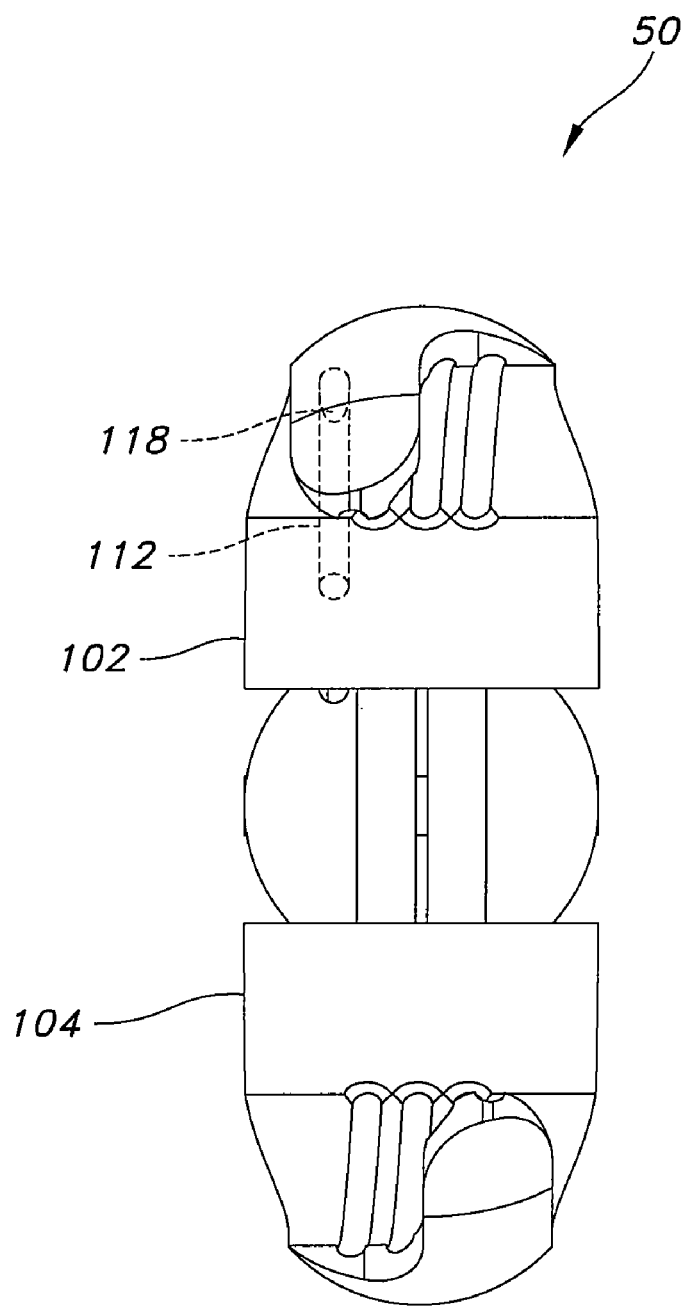
FIG. 16 is an end view of one embodiment of the end effector of FIG. 11.
Figure 17:
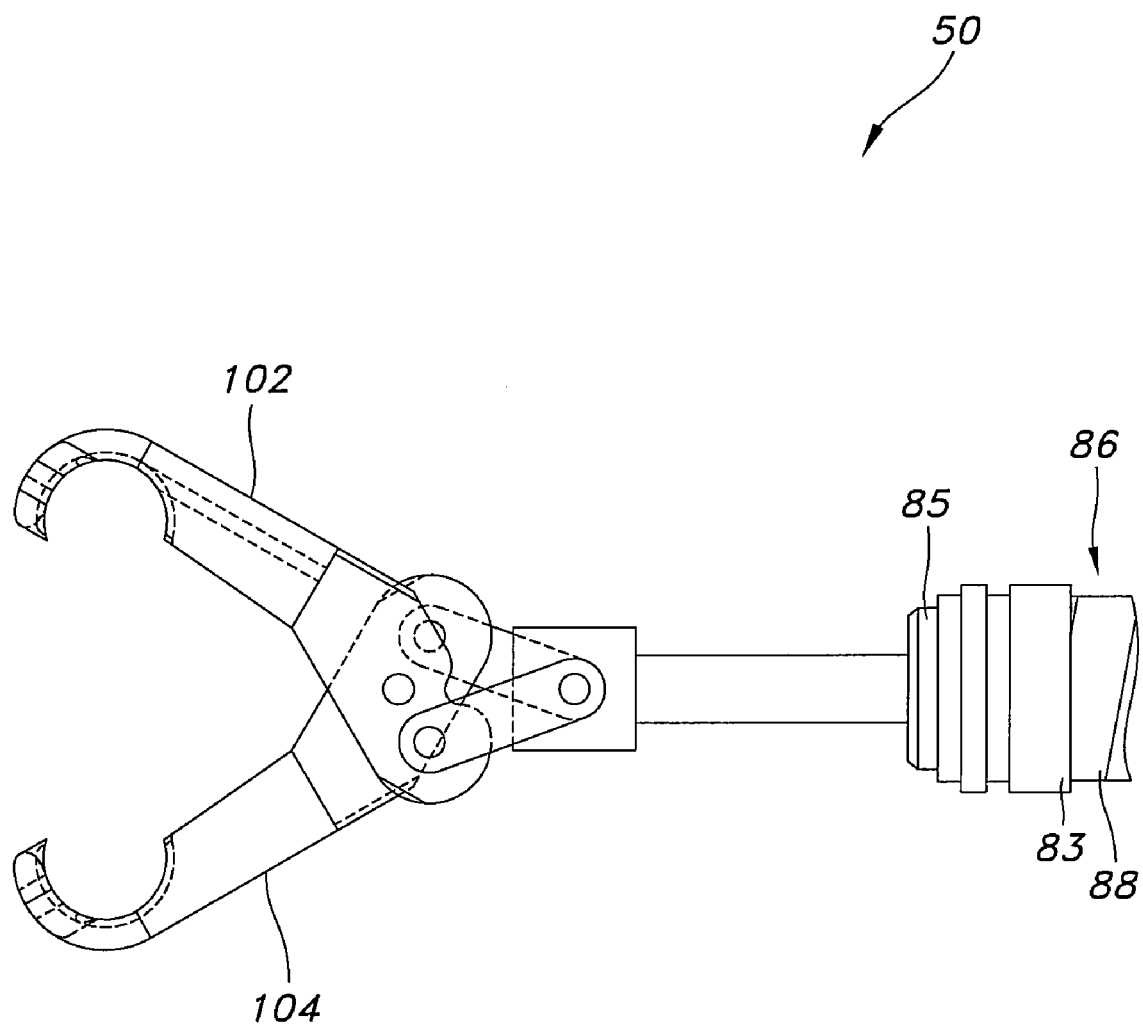
FIG. 17 is a left elevational view of one embodiment of the end effector of FIG. 11 with a clevis removed.
Figure 18:
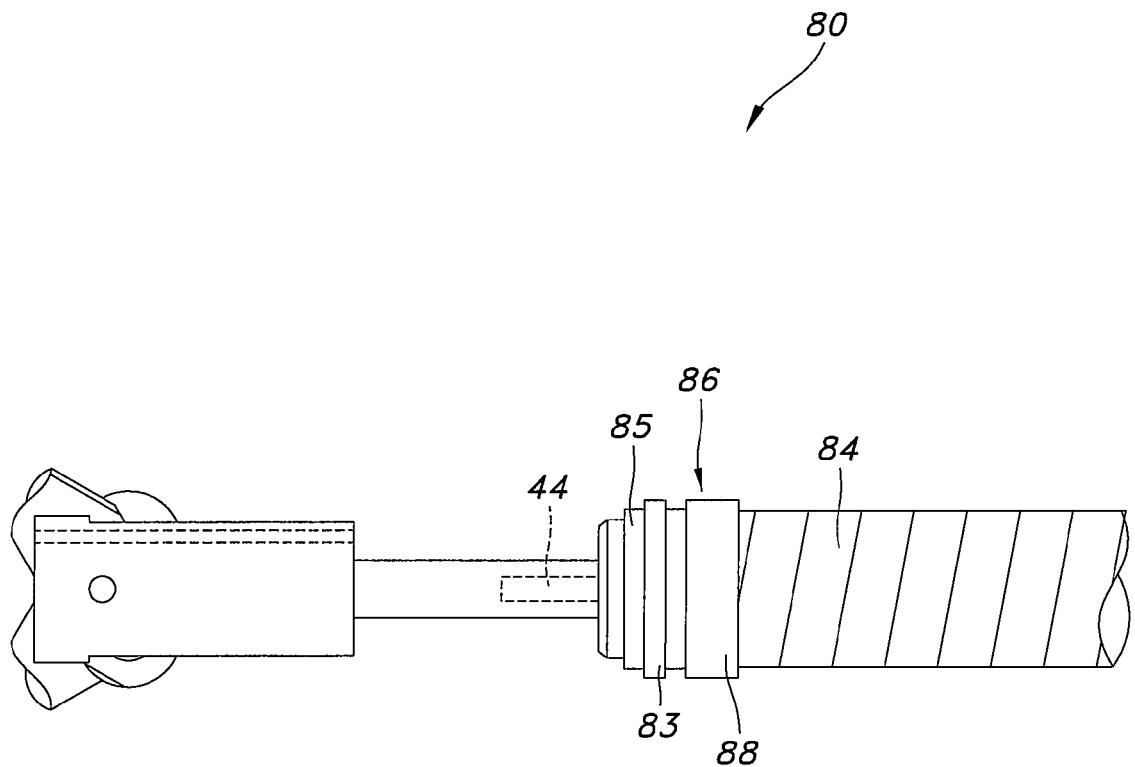
FIG. 18 is a left elevational view of one embodiment of a coupling between the end effector and the shaft assembly of the surgical instrument of FIG. 11.

As described above, the end effector 100 may be utilized with any suitable surgical instrument. FIG. 10 illustrates an embodiment of one such surgical instrument 20. The surgical instrument 20 may include the end effector 100, a shaft assembly 22, and a hand piece 24. In at least one embodiment, the shaft assembly 22 may comprise a flexible shaft of an endoscopic surgical instrument wherein at least portions of the end effector 100 and the shaft assembly 22 may be configured to be positioned within and/or inserted through a working channel of an endoscope. The hand piece 24 may be configured to be grasped by a surgeon and, in at least one embodiment, the hand piece 24 may comprise a pistol grip including the stationary member 26 and movable member, or trigger, 28. In use, as described in greater detail below, the trigger 28 may be moved toward a stationary member 26 as indicated by arrow 27, for example, in order to operate the end effector within a surgical site.

In various embodiments, referring to FIGS. 11-17, the jaw members 102 and 104 may be movably coupled to the housing, or clevis, 106 such that they may be moved, or pivoted, between open and closed positions about pivot pin 58. In use, the jaw members 102 and 104 may be positioned in their closed, or at least partially closed, positions before they are inserted into a surgical site through a trocar, for example. In various embodiments, the jaw members 102 and 104 may be configured such that they may be positioned within and/or inserted through a working channel of an endoscope. Once positioned within the surgical site, the jaw members 102 and 104 may then be reopened. In their open position, the jaw members 102 and 104 may be positioned on, or relative to, the targeted soft tissue within the surgical site. Thereafter, in at least one embodiment, the jaw members 102 and 104 may be pivoted into their closed position to hold the soft tissue therebetween. In various embodiments, the jaw members 102 and 104 may have an interlocking rat's teeth 120, 122 style interface at their distal ends, as shown.

Figure 19:
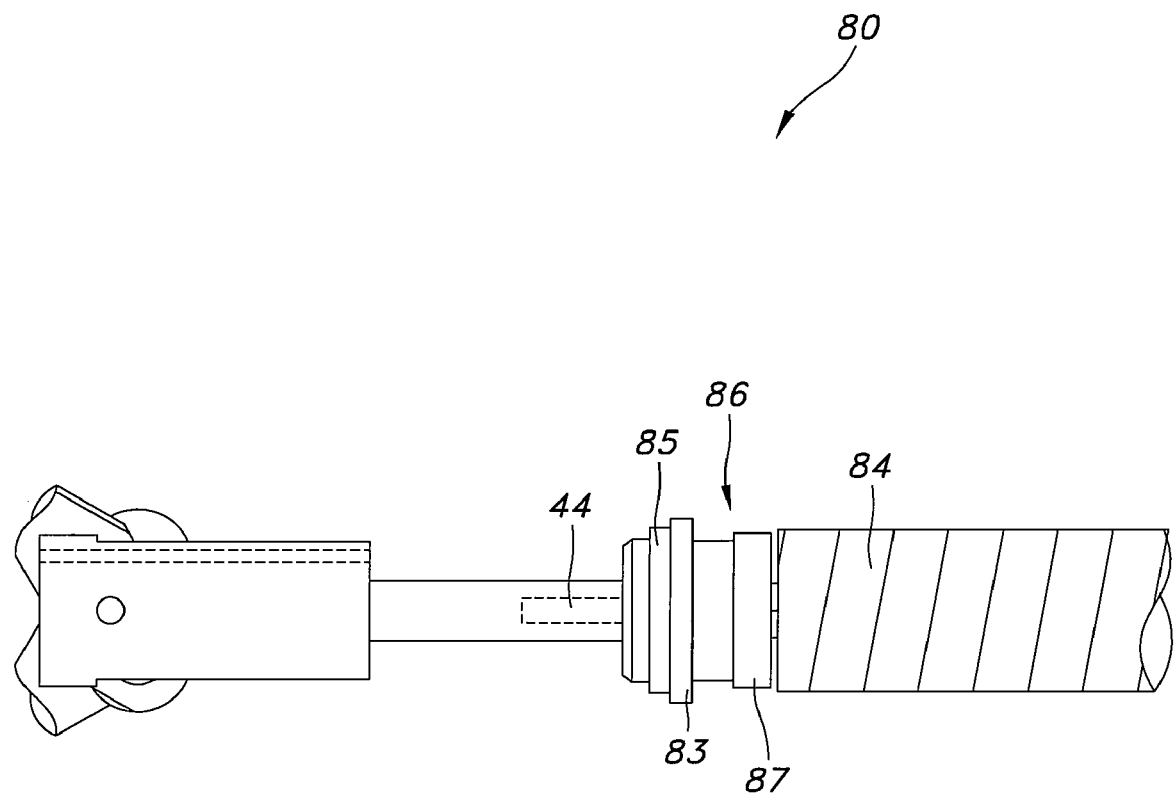
FIG. 19 is a left elevational view of the coupling of FIG. 11 with additional components removed.

In order to more easily position the end effector 100, the shaft assembly extending between the end effector 100 and the hand piece 24 may be flexible. In at least one embodiment, referring to FIG. 11, the shaft assembly 80 may include a flexible elongate member 82 and a flexible coil spring 84 positioned therearound. In various embodiments, referring to FIGS. 15-19, a surgical instrument may further include an adapter assembly 86 for operably connecting the end effector 100 to the shaft assembly 80. In at least one embodiment, the adapter assembly 86 may include a ring capture 88 which may include an aperture therein, or any other suitable feature, for receiving and retaining an end of the coil spring 84. The adapter assembly 86 may further include a bushing coupler 83 which may include projection 85, or any other suitable feature, which may be fixedly connected to the housing 106. In addition to the above, the adapter assembly 86 may also include inner housing coupler 87 (FIG. 19) which may be configured to connect the ring capture 88 to the bushing coupler 83 such that the end effector 100 is correspondingly coupled to the shaft assembly 80.

In order to move the jaw members 102 and 104 between their open and closed positions as described above, a trigger 28 of the hand piece 24 may be pivoted relative to the stationary member 26 such that the trigger 28 may displace an actuator, or rod, 44 (FIG. 10) relative to shaft 22. In various embodiments, the actuator rod 44 may be round, or any other suitable shape, and may be either solid or tubular. In either event, referring to FIG. 14, the actuator rod 44 may be operably engaged with an actuator 46 such that, when the trigger 28 is pivoted toward the stationary member 26 as described above, the actuator rod 44 and the actuator 46 may be slid proximally such that the actuator 46 pulls on jaw links 53 and 55. When jaw links 53 and 55 are pulled proximally, jaw links 53 and 55 may apply a force to jaws 102 and 104, respectively, such that they are pivoted about pivot pin 58 into their closed positions. In order to move jaws 102 and 104 into their open positions, the trigger 28 may be moved away from the stationary portion 26 and, correspondingly, the actuator rod 44 and the actuator 46 may be moved distally by the trigger 28. Similarly, the actuator 46 may move links 53 and 55 distally such that links 53 and 55 apply a force to jaws 102 and 104 and rotate them about pivot pin 58 in the opposite, or open, direction. Now referring to another example embodiment illustrated in FIGS. 20 and 21, when a trigger 28' is pivotally moved (e.g., squeezed) in the direction indicated by arrow 29, the actuator rod 44 may be moved in the direction indicated by arrow 47, and the first and second jaw members 102 and 104 may close in the direction indicated by arrow 49. When the trigger 28' is pivotally moved (e.g., released) in the direction indicated by arrow 31, the actuator rod 44 may be moved in the direction indicated by arrow 45, and the first and second jaw members may open in the direction indicated by arrow 51.

Further to the above, in various embodiments, at least a portion of the proximal end of the actuator rod 44 may be fixedly received in a shaft collar 66' (FIG. 21) such that, when the collar 66' is moved by the trigger 28', the actuator rod 44 may be moved proximally and distally as described above. In at least one embodiment, the trigger 28' may be operably engaged with a pin 67' in the shaft collar 66' such that the rotational movement of the trigger 28' may be converted to translational movement of the shaft collar 66'. More particularly, although not illustrated, the trigger 28' may include a cam slot which is configured to receive a pin 67' such that, when the trigger 28' is rotated as described above, the sidewalls of the slot may motivate the shaft collar 66', and the actuator rod 44 operably engaged therewith, along a path defined by the housing portion 65'. In various embodiments, although not illustrated, the hand piece 24' may further include a biasing member, or spring, which is configured to bias the trigger 28', and the jaw members 102 and 104, into one of a closed or open position.

Figure 21:
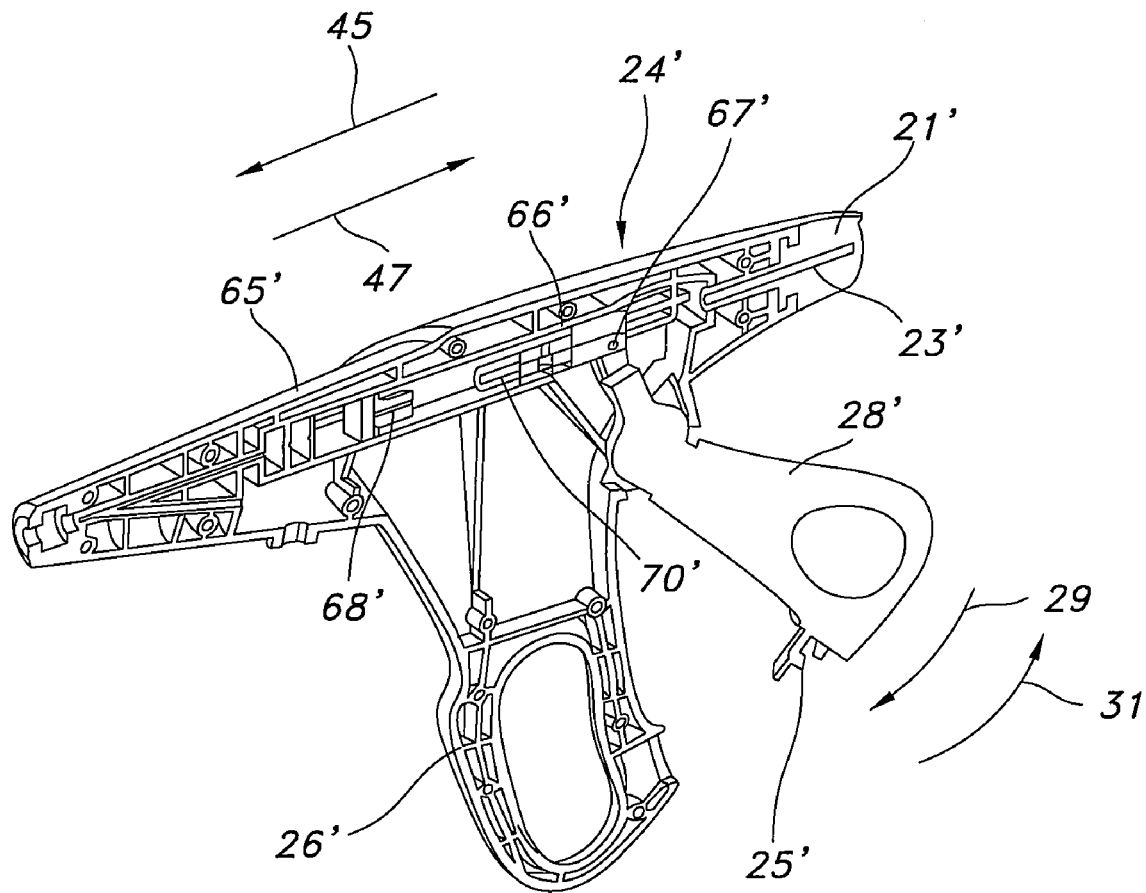
FIG. 21 is a cross-sectional view of one embodiment of a hand piece of the surgical instrument of FIG. 20.

In at least one embodiment, referring to FIG. 21, the hand piece 24' may further include the spring holders 68' and 70' where the spring may be positioned therebetween. In various embodiments, the shaft collar 66' may be connected to one of the spring holders 68' and 70' and the other of the spring holders 68' and 70' may be connected to the housing portion 65'. In such embodiments, when the shaft collar 66' is moved relative to the housing portion 65', one of the spring holders 68' and 70' may be moved relative to the other such that the spring is placed in either tension or compression and may apply a spring force to the trigger 28'. In at least one embodiment, when the trigger 28' is released from its closed position as indicated by arrow 31, the spring force may bias the trigger 28' into its open position, as indicated by arrow 29. In various other embodiments, although not illustrated, the trigger 28' may be biased into its closed position or any other suitable position. In at least one embodiment, the trigger 28' may further include a latch 25' which may be configured to hold the trigger 28' to the stationary portion 26' against the biasing force of the spring.

Figure 20:
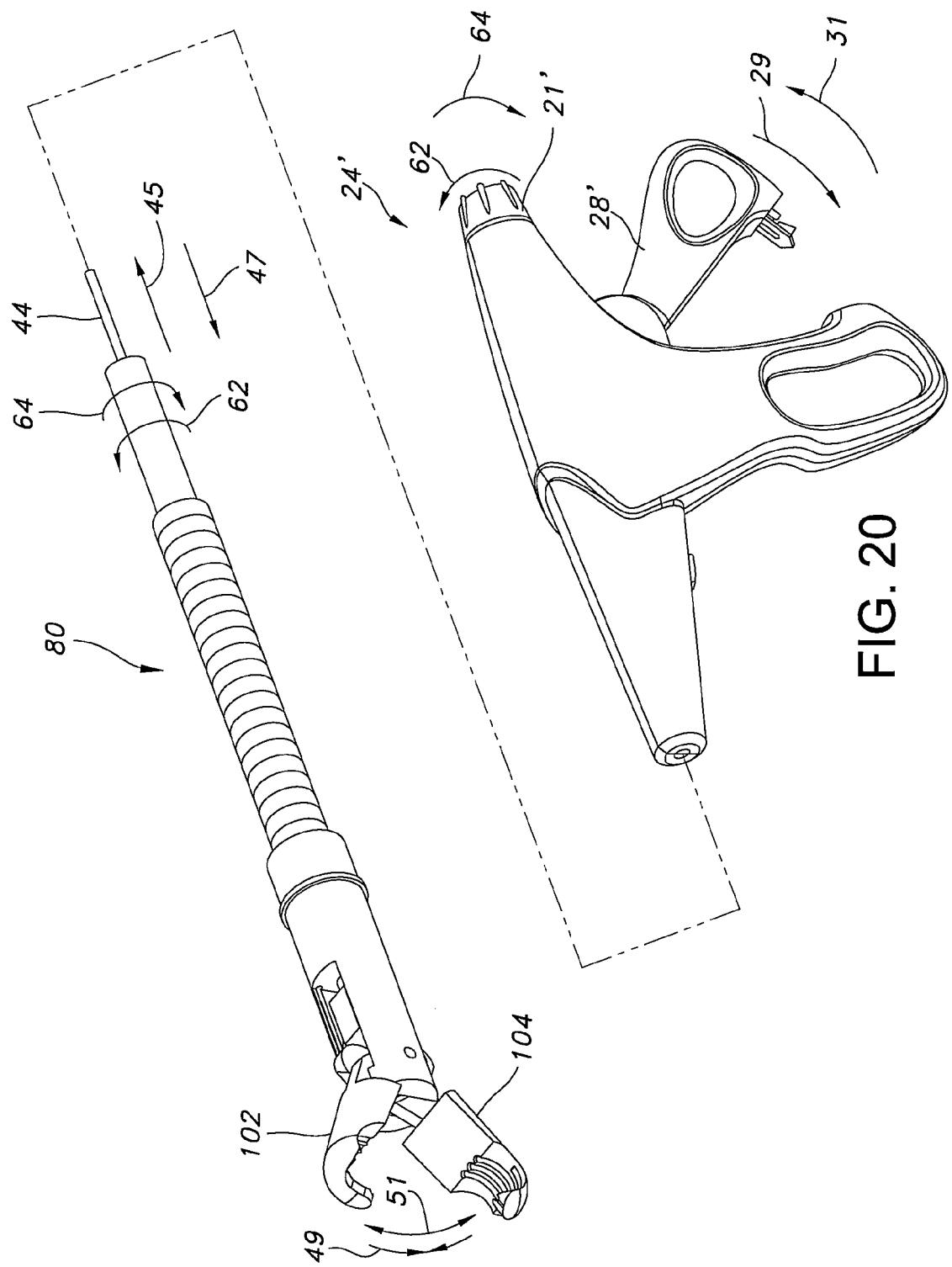
FIG. 20 is a perspective view of one embodiment of a surgical instrument.

In various embodiments, referring to FIG. 10, the hand piece 24 may include a rotation knob 21 and, similarly, referring to FIG. 20, the hand piece 24' may include the rotation knob 21', where the rotation knobs 21 and 21' may be configured to rotate an end effector of their respective surgical instruments relative to the hand pieces 24 and 24'. In various embodiments, referring to FIGS. 20 and 21, a portion of the actuator rod 44 may be slidably received within an aperture (not shown) in the rotation knob 21' wherein at least one of the actuator rod 44 and the aperture may include a non-circular profile. In such embodiments, the non-circular profile may allow the actuator rod 44 to be rotated by the knob 21' yet allow the actuator rod 44 to slide relative thereto when it is moved proximally and distally by the trigger 28', as described above. In at least one embodiment, when the rotation knob 21' is rotated in the direction indicated by an arrow 62, the end effector 100 may also be rotated in the direction indicated by the arrow 62. Similarly, when the rotation knob 21' is rotated in the direction indicated by and arrow 64, the end effector 100 may be rotated in the direction indicated by the arrow 64. As a result of the above, the jaw members 102 and 104 may be rotated within the surgical site and may be more accurately positioned by a surgeon.

In various embodiments, surgical instruments utilizing various embodiments of the end effector 100 may be employed in conjunction with a flexible endoscope, such as a GIF-100 model available from Olympus Corporation, for example. In at least one such embodiment, the endoscope, a laparoscope, or a thoracoscope, for example, may be introduced into the patient trans-anally through the colon, the abdomen via an incision or keyhole and a trocar, or trans-orally through the esophagus, for example. These devices may assist the surgeon to guide and position the electrical ablation system near the tissue treatment region to treat diseased tissue on organs such as the liver, for example. In another embodiment, these devices may be positioned to treat diseased tissue near the gastrointestinal (GI) tract, esophagus, and/or lung, for example. In various embodiments, the endoscope may comprise a flexible shaft where the distal end of the flexible shaft may comprise a light source, a viewing port, and at least one working channel. In at least one such embodiment, the viewing port may transmit an image within its field of view to an optical device such as a charge coupled device (CCD) camera within the endoscope, for example, so that an operator may view the image on a display monitor (not shown).

While several embodiments have been illustrated and described, and while several illustrative embodiments have been described in considerable detail, the embodiments are not intended to restrict or in any way limit the scope of the appended claims to such detail. Additional advantages and modifications may readily appear to those skilled in the art. Those of ordinary skill in the art will readily appreciate the different advantages provided by these various embodiments.

While several embodiments have been described, it should be apparent, however, that various modifications, alterations and adaptations to those embodiments may occur to persons skilled in the art with the attainment of some or all of the advantages of the embodiments. For example, according to various embodiments, a single component may be replaced by multiple components, and multiple components may be replaced by a single component, to perform a given function or functions. This application is therefore intended to cover all such modifications, alterations and adaptations without departing from the scope of the appended claims.

The devices disclosed herein may be designed to be disposed of after a single use, or they may be designed to be used multiple times. In either case, however, the device may be reconditioned for reuse after at least one use. Reconditioning may include a combination of the steps of disassembly of the device, followed by cleaning or replacement of particular pieces, and subsequent reassembly. In particular, the device may be disassembled, and any number of particular pieces or parts of the device may be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of the present application.

Preferably, the embodiments described herein will be processed before surgery. First, a new or used instrument is obtained and, if necessary, cleaned. The instrument may then be sterilized. In one sterilization technique, the instrument is placed in a closed and sealed container, such as a plastic or TYVEK® bag. The container and instrument are then placed in a field of radiation that may penetrate the container, such as gamma radiation, x-rays, or higher energy electrons. The radiation kills bacteria on the instrument and in the container. The sterilized instrument may then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The embodiments are not to be construed as limited to the particular embodiments disclosed. The embodiments are therefore to be regarded as illustrative rather than restrictive. Variations and changes may be made by others without departing from the scope of the claims. Accordingly, it is expressly intended that all such equivalents, variations and changes that fall within the scope of the claims be embraced thereby.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical applications to thereby enable one of ordinary skill in the art to utilize the various embodiments and with various modifications as are suited to the particular use contemplated. It is intended that the claims submitted herewith define the overall scope.

Various embodiments are directed to a surgical device comprising an end effector, wherein the end effector comprises: a first jaw member defining a first groove; a second jaw member defining a second groove; wherein the first jaw member and the second jaw member are selectively pivotable between an open position and a closed position; wherein the first groove and the second groove align to form a combined helical groove when the first jaw member and the second jaw member are in the closed position; and wherein the first jaw member defines a wire opening aligned with the first groove; and a beveled edge directed distally and substantially parallel to a distal portion of the wire opening, wherein the beveled edge is fixedly coupled to the first jaw member such that it cuts a wire when the wire is retracted proximally through the wire opening.

What is claimed is:

1. A surgical device comprising an end effector, wherein the end effector comprises:
   a first jaw member defining a first groove;
   a second jaw member defining a second groove;
   wherein the first jaw member and the second jaw member are selectively pivotable between an open position and a closed position;
   wherein the first groove and the second groove align to form a combined helical groove when the first jaw member and the second jaw member are in the closed position; and
   wherein the first jaw member defines a wire opening aligned with the first groove; and
   a beveled edge directed distally and substantially parallel to a distal portion of the wire opening, wherein the beveled edge is fixedly coupled to the first jaw member such that it cuts a wire when the wire is retracted proximally through the wire opening.

2. The surgical device of claim 1, wherein a distal edge of the first jaw member and a distal edge of the second jaw member define an interlocking pattern.

3. The surgical device of claim 1, further comprising a shaft portion pivotably connected to the first jaw member and the second jaw member.

4. The surgical device of claim 3, wherein the shaft portion comprises a shaft wire opening aligned with the wire opening.

5. The surgical device of claim 4, further comprising a handle, wherein the handle comprises a trigger, and wherein the trigger is actuatable to transition the first jaw member and the second jaw member from the open position to the closed position.

6. The surgical device of claim 1, wherein the first groove and the second groove are positioned at distal portions of the first and second jaw members.

7. The surgical device of claim 1, wherein the first jaw member and the second jaw member comprise a groove section and a tooth section, and wherein the tooth section is positioned distally relative to the groove section.

\* \* \* \* \*